United States Patent

Haneishi et al.

[11] Patent Number: 5,041,423
[45] Date of Patent: Aug. 20, 1991

[54] ANTIBIOTICS OF THE MUREIDOMYCIN GROUP, THEIR PREPARATION, AND THEIR THERAPEUTIC USE

[75] Inventors: Tatsuo Haneishi; Masatoshi Inukai; Keiko Shimizu; Fujio Isono; Yoshiharu Sakaida; Takeshi Kinoshita, all of Hiromachi, Japan

[73] Assignee: Sankyo Company, Limited, Tokyo, Japan

[21] Appl. No.: 273,199

[22] Filed: Nov. 17, 1988

[30] Foreign Application Priority Data

Nov. 20, 1987 [JP] Japan .................. 62-293352
Nov. 20, 1987 [JP] Japan .................. 62-293353

[51] Int. Cl.$^5$ .................. A61K 37/02; C07K 5/08; C07K 5/10
[52] U.S. Cl. .................. 514/18; 514/19; 530/330; 530/331
[58] Field of Search .................. 530/330, 331; 514/18, 514/19

[56] References Cited

U.S. PATENT DOCUMENTS 4,670,542  6/1987  Benz et al. .................. 530/331
4,722,924  2/1988  Baldwin .................. 530/331
4,748,155  5/1988  Sisto et al. .................. 514/18

*Primary Examiner*—Lester L. Lee
*Attorney, Agent, or Firm*—Frishauf, Holtz, Goodman & Woodward

[57] ABSTRACT

New antibiotics of the mureidomycin group have the formula

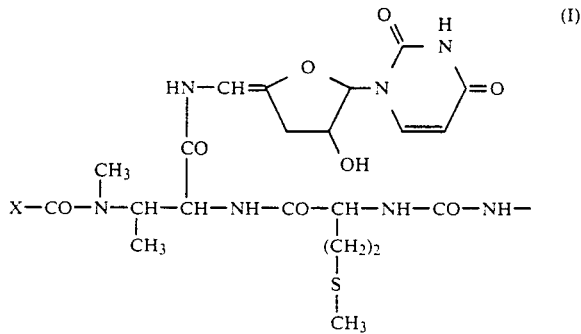

wherein X represents the group (Abstract continued on next page.)

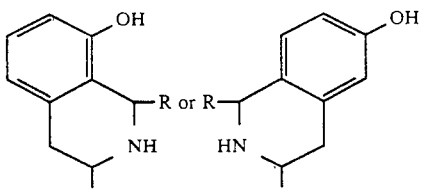

and wherein R represents hydrogen, an alkyl group having from 1 to 10 carbon atoms, an alkenyl group having from 2 to 7 carbon atoms, an alkynyl group having from 3 to 7 carbon atoms, an aryl group having from 6 to 10 carbon atoms, an aralkyl group having from 7 to 10 carbon atoms, or one of the said aryl or aralkyl groups substituted with at least one substituent selected from halogen and alkyl groups having from 1 to 5 carbon atoms. The compound in which X represents 8-hydroxy-1,2,3,4-tetrahydroisoquinolin-3-yl is named mureidomycin E and the compound in which X represents 6-hydroxy-1,2,3,4-tetrahydroisoquinolin-3-yl is named mureidomycin F. This group of compounds and their pharmaceutically acceptable esters and salts are useful as antibiotics for the treatment of bacterial infections. Mureidomycins E and F can be obtained by fermentation of a suitable Streptomyces strain, in particular *Streptomyces flaviodovirens* SANK 60486 (BIKOKEN JOHKI 1347; FERM BP-1347). Alternatively, all of the compounds can be obtained synthetically by reacting the previously known compound mureidomycin A with an aldehyde of the formula

R—CHO.

31 Claims, 12 Drawing Sheets

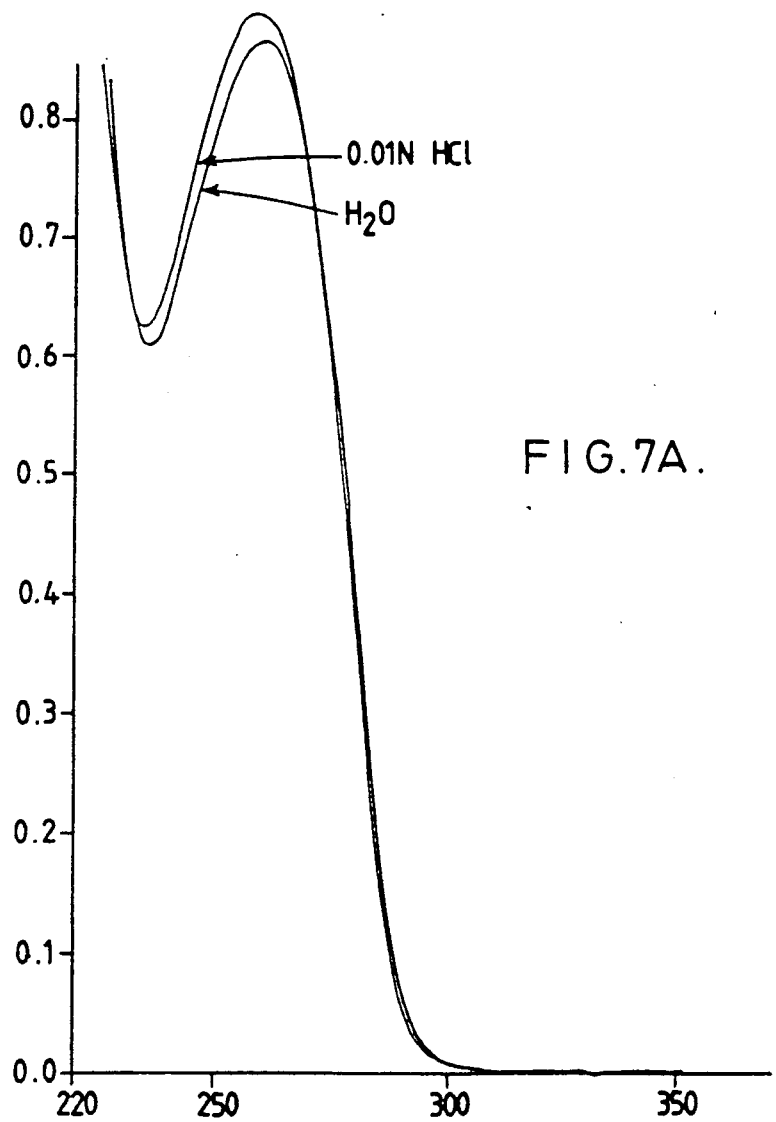

ANTIBIOTICS OF THE MUREIDOMYCIN GROUP, THEIR PREPARATION, AND THEIR THERAPEUTIC USE

BACKGROUND TO THE INVENTION

The present invention relates to certain novel antibiotics of the mureidomycin group, and also provides methods for preparing them and an antibacterial composition containing at least one of them as the active ingredient.

As resistance to conventional antibiotics becomes increasingly established in common strains of pathogenic bacteria, the need for a wider variety of antibiotics for use in the fight against such bacteria becomes ever more crucial. Although this need can be, and sometimes is, met by chemical modification of existing classes of antibiotics, the discovery of a wholly new class of antibiotics leads to exciting possibilities in the treatment of diseases caused by pathogenic bacteria.

Such a new class of antibiotics, named the "mureidomycins", is disclosed in our previous U.S. patent application Ser. No. 51,665 filed on May 18, 1987 and now abandoned which has been replaced by Continuation-in-part application Ser. No. 07/253,450 filed Oct. 4, 1988. In this we have disclosed the isolation of the first four members of this class, mureidomycins A, B, C and D, from the fermentation broth produced by a then newly discovered microorganism, Streptomyces flavidovirens SANK 60486 (BIKOKEN JOHKI 1347; FERM BP-1347).

We have now discovered two new members of this class of antibiotics, herein named "mureidomycins E and F", together with their salts and esters and certain other derivatives, which are particularly effective against Gram-negative bacteria, most especially strains of the genus Pseudomonas.

Mureidomycins E and F can also be isolated from the fermentation broth of Streptomyces strain SANK 60486. Alternatively, these two new mureidomycins, as well as certain of their derivatives, can be prepared by subjecting mureidomycin A to chemical reaction.

We have also discovered a further group of compounds, herein named "mureidomycins AP to FP", which are derivatives of and can be prepared from mureidomycins A to F, respectively. These compounds, and their salts and esters, are of use as synthetic intermediates in the preparation of other mureidomycins.

BRIEF SUMMARY OF THE INVENTION

It is, therefore, an object of the present invention to provide, as a new composition of matter, certain new compounds having useful antibacterial activities.

It is a further object of the invention to provide a pharmaceutical composition containing at least one such compound as the active component, and a method for the treatment or prophylaxis of bacterial infections employing at least one such compound as the active component.

Mureidomycins A to F referred to herein can be represented by the following planar structural formula:

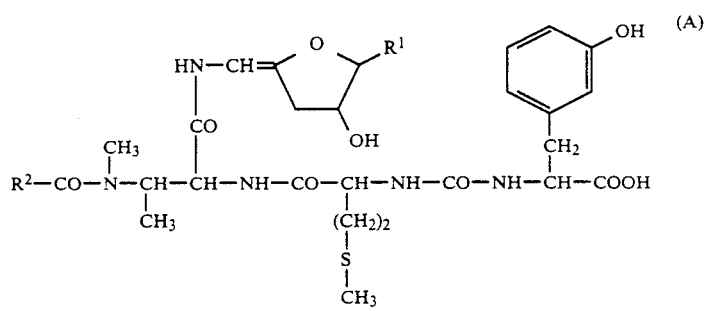

wherein:
for Mureidomycin A, $R^1$ represents 2,4-dioxopyrimidin-1-yl and $R^2$ represents α-amino-3-hydroxyphenethyl;
for Mureidomycin B, $R^1$ represents 2,4-dioxodihydropyrimidin-1-yl and $R^2$ represents α-amino-3-hydroxyphenethyl;
for Mureidomycin C, $R^1$ represents 2,4-dioxopyrimidin-1-yl and $R^2$ represents α-glycylamino-3-hydroxyphenethyl;
for Mureidomycin D, $R^1$ represents 2,4-dioxodihydropyrimidin-1-yl and $R^2$ represents α-glycylamino-3-hydroxyphenethyl;
for Mureidomycin E, $R^1$ represents 2,4-dioxopyrimidin-1-yl and $R^2$ represents 8-hydroxy-1,2,3,4-tetrahydroisoquinolin-3-yl: and
for Mureidomycin F, $R^1$ represents 2,4-dioxopyrimidin-1-yl and $R^2$ represents 6-hydroxy-1,2,3,4-tetrahydroisoquinolin-3-yl.

Thus, the invention provides as new compounds, mureidomycins E and F and derivatives thereof which can be represented by the following planar structural formula:

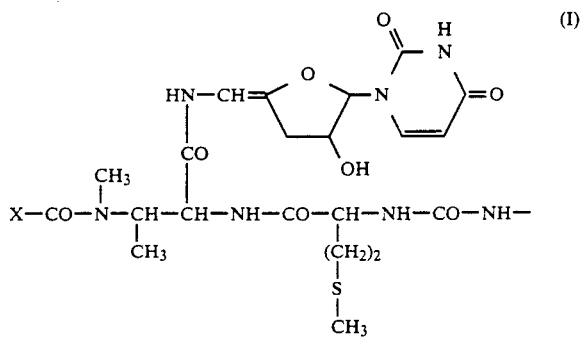

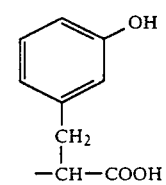

wherein X represents the group

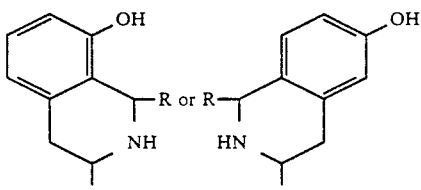

wherein R represents hydrogen, alkyl alkenyl, alkynyl, aryl or aralkyl. Mureidomycin E is the compound of the above formula (I) wherein X represents the group

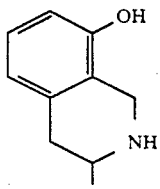

(i.e. the 8-hydroxy-1,2,3,4-tetrahydroisoquinolin-3-yl group) and mureidomycin F is the compound of the above formula (1) wherein X represents the group

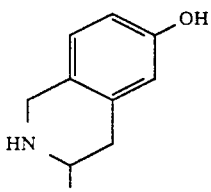

(i.e. the 6-hydroxy-1,2,3,4-tetrahydroisoquinolin-3-yl group).

The invention also provides, as new compounds, mureidomycins AP to FP which can be represented by the following planar structural formula:

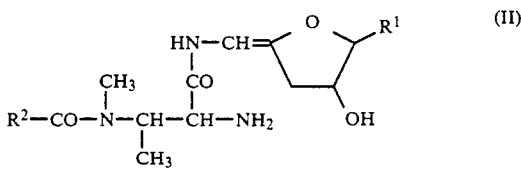

wherein $R^1$ and $R^2$ have the same meanings as before.

The invention also provides pharmaceutically acceptable salts and esters of the above compounds of formula (I) and salts of those of formula (II).

The invention further provides a process for producing mureidomycin E or F or a salt or ester thereof, by cultivating a mureidomycin E or F producing microorganism of the genus Streptomyces in a culture medium therefor and isolating mureidomycin E or F or a salt thereof from the cultured broth and optionally salifying, desalifying or esterifying the compound thus isolated.

The invention still further provides a pharmaceutical composition comprising such a mureidomycin E or F or a salt or ester thereof in admixture with a pharmaceutically acceptable carrier or diluent.

The invention yet further provides a method for the treatment or prophylaxis of bacterial infections by administering such a mureidomycin E or F or a salt or ester thereof to an animal, which may be human or non-human.

BRIEF DESCRIPTION OF THE DRAWINGS

FIGS. 7A and 7B show the ultraviolet absorption spectrum of mureidomycin A;

DETAILED DESCRIPTION OF THE INVENTION

Figure 1:
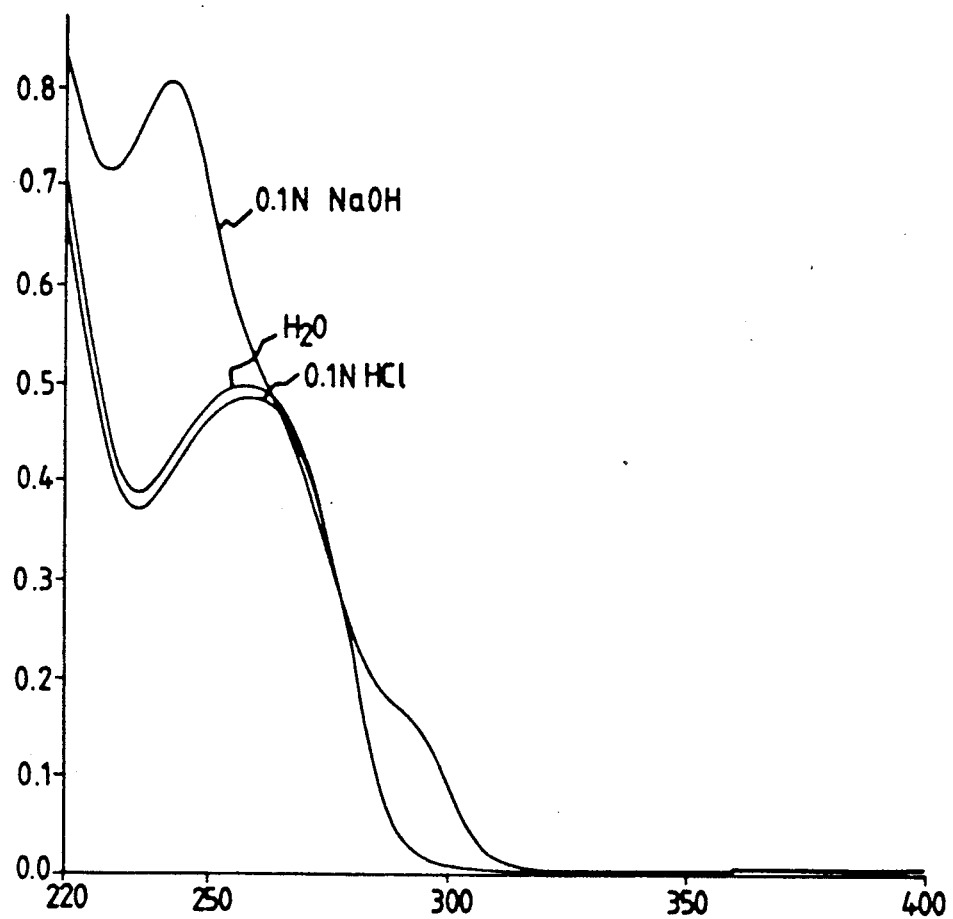
FIG. 1 shows the ultraviolet absorption spectrum of mureidomycin E.

In the above formula (1), where R is alkyl, it may suitably be straight or branched $C_1$-$C_{10}$, preferably $C_1$-$C_5$, most preferably $C_1$-$C_3$ alkyl, for example methyl, ethyl, propyl, isopropyl, butyl, isobutyl, t-butyl, pentyl, isopentyl, neopentyl, t-pentyl, hexyl, 1,1-dimethylbutyl, 1,3-dimethylbutyl, heptyl, octyl, 2-ethylhexyl, nonyl or decyl.

Where R is alkenyl, it may suitably be straight or branched $C_2$-$C_7$, more preferably $C_2$-$C_4$ alkenyl, for example vinyl, allyl, methallyl, 2-butenyl, 3-butenyl, 3-pentenyl, 4-hexenyl or 5-heptenyl.

Where R is alkynyl, it may suitably be straight or branched $C_3$-$C_7$, more preferably $C_3$-$C_4$ alkynyl, for example ethynyl, 1-propynyl, 2-propynyl, 2-butynyl, 3-pentynyl, 3-hexynyl or 4-heptynyl.

Where R is aryl, it may suitably be $C_6$-$C_{10}$ aryl, for example phenyl or naphthyl, and more preferably phenyl.

Where R is aralkyl, it may suitably be $C_7$-$C_{10}$, more preferably $C_7$-$C_8$ aralkyl, for example benzyl, phenetyl, α-methylbenzyl, 3-phenylpropyl or 4-phenylbutyl.

Where R is aryl or aralkyl, the aryl nucleus can be unsubstituted or may optionally carry one or more substituents, such as straight or branched $C_1$-$C_5$ alkyl (e.g. methyl, ethyl, propyl, butyl or pentyl) or halogen (e.g. chlorine, fluorine or bromine).

Preferably R is hydrogen, $C_1$-$C_{10}$ alkyl, phenyl, ($C_1$-$C_5$ alkyl)phenyl or halophenyl, and most preferably R is hydrogen, $C_1$-$C_5$ alkyl or phenyl.

Since the compounds of formula (I) are amphoteric in character, they are capable of forming salts and esters, and these salts and esters also form part of the present invention. The nature of such salts and esters is not critical, except that, where they are to be used for medicinal or veterinary purposes, they must be medicinally acceptable, i.e. they must not, or must not to a significant extent, either have increased toxicity or have reduced activity, as compared with the free unsalified or unesterified compound.

Examples of suitable acids for the formation of such salts include inorganic acids, such as hydrochloric, sulfuric or phosphoric acid; organic carboxylic acids, such as acetic, citric, tartaric malonic, maleic, malic, fumaric, itaconic, citraconic or succinic acid; and organic sulfonic acids, such as methanesulfonic, benzenesulfonic, naphthalenesulfonic or p-toluenesulfonic acid.

The carboxy group present in the said compounds may also form salts with appropriate bases. Examples of such salts include salts with metals, especially alkali and alkaline earth metals, such as the lithium, sodium potassium, calcium and magnesium salts the ammonium salts, salts with organic amines, such as cyclohexylamine, diisopropylamine or triethylamine, and salts with basic amino acids, such as lysine or arginine.

Examples of suitable esters of the said compounds of formula (I) include: $C_1$-$C_6$, more preferably $C_1$-$C_4$, alkyl esters for example the methyl, ethyl, propyl, isopropyl butyl, isobutyl sec-butyl, t-butyl, pentyl and hexyl esters; aralkyl, including diarylalkyl, esters, such as the benzyl, p-nitrobenzyl and benzhydryl esters; alkoxycarbonylalkyl esters, in which the alkoxy and alkyl moieties suitably each have from 1 to 4 carbons especially alkoxycarbonylmethyl esters such as the ethoxycarbonylmethyl and t-butoxycarbonylmethyl esters; alkoxycarbonyloxyalkyl esters in which the alkoxy and alkyl moieties suitably each have from 1 to 4 carbons, especially 2-alkoxycarbonyloxyethyl esters such as the 2-methoxycarbonyloxyethyl, 2-ethoxycarbonyloxyethyl and 2-t-butoxycarbonyloxyethyl esters; and other specific esters, such as the phthalidyl, substituted phthalidyl, phenacyl, substituted phenacyl (e.g. p-nitrophenacyl) and (5-methyl-2-oxo-1,3-dioxolen-4-yl)methyl esters.

Mureidomycins E and F and salts thereof are produced by the cultivation of a Streptomyces strain herein identified as Streptomyces sp. SANK 60486, and which has the following mycological properties. These characteristics were determined by cultivation on various media prescribed by the ISP (International Streptomyces project) or with the media recommended by S. A. Waksman in Volume 2 of "The Actinomycetes", in all cases at a temperature of 28° C., except where otherwise stated.

1. Morphological characteristics

Generally, on an agar medium, the substrate hyphae of the microorganism branch and elongate well and the aerial hyphae of the microorganism branch simply. The spore chain forms straight to curved lines. It is observed that the number of spores formed on a spore chain are mostly from ten to fifty, but may be more. The spores are ellipsoidal, in the size range from 0.5–0.8 $\mu m \times 0.7$–1.1 $\mu m$, and with a smooth surface. No special organs, such as wheel axle branching of the aerial hyphae, sclerotia, sporangia and the like, were observed.

2. Culture characteristics on various media

After culturing on various kinds of culture media at 28° C. for 14 days, the properties are shown in Table 1. Representation of the color tones is shown by using the color tip numbers given in the "Guide to Color Standard" edited by Nippon Shikisai Kenkyusho.

In this Table, the following abbreviations are used:
G: growth; AM: aerial mycelium; R: reverse; SP: soluble pigment.

TABLE 1

| Culture medium | Item | Properties of SANK 60486 |
| --- | --- | --- |
| Sucrose nitrate agar | G | Limited, flat, yellowish gray (1-9-10) |
|  | AM | Well formed, powdery, yellowish gray (1-9-10) |
|  | R | Pale yellowish orange (2-9-9) |
|  | SP | Not produced |
| Glucose asparagine agar | G | Good, flat, light brown (2-8-9) |
|  | AM | Well formed, powdery, pale yellowish orange (2-9-9) |
|  | R | Yellowish brown (4-7-9) |
|  | SP | Not produced |
| Glycerin asparagine agar (ISP 5) | G | Good, protuberant, pale yellowish orange (2-7-9) |
|  | AM | Plentiful, powdery, pale yellowish orange (2-9-9) |
|  | R | Yellowish brown (4-7-9) |
|  | SP | Not produced |
| Starch inorganic salt agar (ISP 4) | G | Very good, flat, pale yellowish brown (4-8-9) |
|  | AM | Plentiful, powdery, pale yellowish orange (2-9-9) |
|  | R | Pale yellowish brown (4-8-9) |
|  | SP | Not produced |
| Tyrosine agar (ISP 2) | G | Very good, flat, bright brownish gray (2-8-8) |
|  | AM | Plentiful, powdery, brownish white (1-8-6) |
|  | R | Yellowish brown (4-7-9) |
|  | SP | Not produced |
| Peptone yeast extract iron agar (ISP 6) | G | Very good, rumpled, pale yellowish brown (4-8-9) |
|  | AM | Slighly formed, white |
|  | R | Pale yellowish brown (6-7-9) |
|  | SP | Not produced |
| Nutrient agar (Difco) | G | Very good, flat, pale yellowish orange (2-9-9) |
|  | AM | Well formed, powdery, white |
|  | R | Pale yellowish orange (2-9-9) |
|  | SP | Not produced |
| Yeast germ wheat agar (ISP 2) | G | Very good, flat, pale yellowish brown (4-8-9) |
|  | AM | Plentiful, powdery, yellowish gray (2-8-10) |
|  | R | Yellowish brown (8-6-9) |
|  | SP | Not produced |
| Oatmeal agar (ISP 3) | G | Good, flat, yellowish gray (1-9-10) |
|  | AM | Plentiful, powdery, yellowish gray (1-9-10) |
|  | R | Pale yellowish brown (6-7-9) |
|  | SP | Pale yellowish brown (4-7-8 slightly) |
| Water agar | G | Limited, flat, yellowish gray (1-9-10) |
|  | AM | Limited, powdery, white |
|  | R | Pale yellowish orange (2-9-9) |
|  | SP | Not produced |
| Potato extract carrot extract agar | G | Limited, flat, pale yellowish orange (2-9-9) |
|  | AM | Well formed, powdery, pale yellowish orange (2-9-9) |
|  | R | Pale yellowish orange (2-9-9) |
|  | SP | Not produced |

3. Physiological properties

The physiological properties of strain SANK 60486 are shown in Table 2.

TABLE 2

| | |
| --- | --- |
| Hydrolysis of starch | Positive |
| Liquefaction of gelatin | Positive |
| Reduction of nitrate salt | Positive |
| Coagulation of milk | Positive |
| Peptonization of milk | Positive |
| Temperature range of growth (culture medium 1)* | 6–34° C. |
| Sodium chloride resistance (culture medium 1)* | Growth in 7%, no growth in 10% |
| Decomposition of casein | Positive |

TABLE 2-continued

| | |
|---|---|
| Decomposition of tyrosine | Positive |
| Decomposition of xanthine | Negtive |
| Productivity of melanin-like pigment | |
| (culture medium 2)* | Negative |
| (culture medium 3)* | Negative |
| (culture medium 4)* | Negative |

*Culture medium 1; yeast germ wheat agar (ISP 2);
Culture medium 2; tryptone yeast extract broth (ISP 1);
Culture medium 3; peptone yeast extract iron agar (ISP 6);
Culture medium 4; tyrosine agar (ISP 7).

After culturing on Pridham Gottlieb agar medium (ISP 9) at 28° C. for 14 days, assimilability of carbon sources by strain SANK 60486 is shown in Table 3.

TABLE 3

| | |
|---|---|
| D-Glucose | + |
| L-Arabinose | + |
| D-Xylose | + |
| Inositol | − |
| D-Mannitol | + |
| D-Fructose | + |
| L-Rhamnose | + |
| Sucrose | − |
| Raffinose | − |
| Control | − |

In the above Table:
+ assimilable; − not assimilable.

4. Cell wall constitution

The cell wall of strain SANK 60486 was examined according to the method of B. Becker et al. [Applied Microbiology, 12, 421–423 (1964)]. L,L-Diaminopimelic acid and glycine were detected in it.

Identification of strain SANK 60486 was carried out in accordance with The International Streptomyces project; Bergey's Manual of Determinative Bacteriology, 8th edition; "The Actinomycetes" edited by S. A. Waksman and other recent literature relating to the Streptomycetes.

On the basis of the above data, the strain was identified as a strain of *Streptomyces flavidovirens* and is here referred to as *Streptomyces flavidovirens* SANK 60486 (BIKOKEN JOHKI 1347; FERM BP-1347).

The strain SANK 60486 has been deposited with the Fermentation Research Institute, Agency of Industrial Science and Technology, Ministry of International Trade and Industry, Japan, on Feb. 4, 1986 under the accession number FERM P-8636 and was re-deposited in accordance with the conditions stipulated by the Budapest Treaty with said Fermentation Research Institute on Apr. 17, 1987 under the accession number FERM BP-1347.

It has been established that strain SANK 60486 produces mureidomycins E and F. However, as is well known, the properties of microorganisms falling within the general category of the actinomycetes can vary considerably and such microorganisms can readily undergo mutation, both through natural causes and as the result of induction by artificial means. Accordingly, the process of the present invention embraces the use of any microorganism which can be classified within the genus Streptomyces and which shares with the strain SANK 60486 the characteristic ability to produce mureidomycins E and F.

The microorganism employed in the process of the present invention is preferably a strain of the species *Streptomyces flavidovirens*, and more preferably *Streptomyces flavidovirens* SANK 60486 (FERM BP-1347).

The cultivation of microorganisms of the genus Streptomyces in accordance with the present invention to produce mureidomycins E and F can be performed under conditions conventionally employed for the cultivation of actinomycetes species, preferably in a liquid culture, and desirably with shaking or stirring and aeration. The nutrient medium used for the cultivation is completely conventional and contains such constituents as are commonly used in the cultivation of the actinomycetes. Specifically, the medium should contain one or more assimilable carbon sources suitable examples of which include glucose, maltose, sucrose, mannitol, molasses, glycerol, dextrin, starch, soybean oil and cottonseed oil; one or more assimilable nitrogen sources, suitable examples of which include soybean meal, peanut meal, cottonseed meal, pharmamine, fish meal, corn steep liquor, peptone, meat extract, live yeast, pressed yeast, yeast extract, sodium nitrate, ammonium nitrate or ammonium sulfate; and one or more inorganic salts, such as sodium chloride, phosphates, calcium carbonate and trace metal salts. Where cultivation is effected in a liquid medium, it is generally desirable to incorporate an anti-foaming agent (for example silicone oil, vegetable oil or a suitable surfactant) in the medium.

The cultivation is suitably performed at a substantially neutral pH value and at a temperature of from 20° to 37° C., more preferably at about 22° C.

The production of mureidomycins as cultivation proceeds may be monitored by a variety of conventional microbiological assay techniques for monitoring the production of antibiotics (when they are produced by microbial culture) and which require little or no elaboration here. A suitable technique might be the paper disc-agar diffusion assay (using, for example, a paper disc of diameter about 8 mm produced by Toyo Kagaku Sangyo Co., Ltd) and using, for example, *Pseudomonas aeruginosa* strain SANK 70579 as the test organism.

The amount of mureidomycins produced normally reaches a maximum after cultivation has proceeded for 72–96 hours and it is clearly desirable to separate the mureidomycins from the culture medium no later than the time when this maximum has been reached. However, this period may vary, depending upon the cultivation conditions and techniques, and a shorter or longer period may be appropriate, depending upon the circumstances. The correct cultivation time may readily be assessed for every case by routine experiment, using suitable monitoring techniques, e.g. as described above.

Mureidomycins E and F are mainly released into the liquid portion of the cultured broth and can thus be recovered by removing solid matter, including the mycelium, for example by filtration (preferably using a filter aid such as diatomaceous earth) or by centrifugation. They can then be recovered from the separated liquid portion by conventional techniques and, if desired then purified and/or separated from each other.

The antibiotics, mureidomycins E and F, may he separated, collected and purified by utilizing their physico-chemical properties. For example, suitable methods include: extraction with solvents; ion-exchange through resins, for example, anion exchange resins such as Dowex SBR-P (Dow Chemical Co.) or cation exchange resins such as Dowex 50 W (Dow Chemical Co.) or IRC-50, CG-50 (Rohm & Haas Co.); chromatography through active carbon as the absorbent or through non-ionic absorption resins such as Amberlite XAD-2, XAD-4 or XAD-7 (Rohm and Hass Co.) or Diaion HP 10, HP 20, CHP 20P or HP 50 (Mitsubishi Chemical Industries, Ltd.); and chromatography through silica gel or alumina. Furthermore, separation, collection and purification of the metabolites may be performed by using any one or more of the following operations, which may be combined in any order or repeated, if desired: partition column chromatography over cellulose such as Avicel (Asahi Chemical Industry Co. Ltd.) or Sephadex LH-20 (Pharmacia Co.); gel filtration using Sephadex G-10, G-25, G-50 or G-100 (Pharmacia Co.) or Toyopearl HW-40 (Toyo Soda Manufacturing Co., Ltd ); crystallization; and recrystallization. ("Dowex", "Amberlite", "Diaion", "Avicel", "Sephadex" and "Toyopearl" are all trade marks.)

Depending upon the culture conditions, mureidomycins E and F can exist in the mycelium from the culture and can be extracted therefrom by conventional techniques. For example, they can be extracted with a hydrophilic organic solvent (such as an alcohol or acetone), and then the solvent removed from the extract to leave a residue, which is dissolved in an aqueous medium. The mureidomycins can be extracted from the resulting solution and purified as described above.

Mureidomycins E and F are preferably separated from each other by chromatography.

Where the mureidomycin E or F is isolated in the form of a salt, it may be converted to the free unsalified compound by conventional means, such as the use of ion-exchange resins or of adsorbents for reverse phase chromatography. Equally, the free unsalified compound may be salified by conventional means, for instance by treatment with an appropiate acid, such as one of those listed above, or with an appropiate base (e.g., a metal hydroxide or carbonate, such as sodium or potassium hydroxide or sodium or calcium carbonate). Esters may be prepared by conventional esterification procedures, such as by reaction with an appropiate alcohol under acid catalysis.

Mureidomycins E and F thus obtained have the physical and chemical properties described below.

Figure 2:
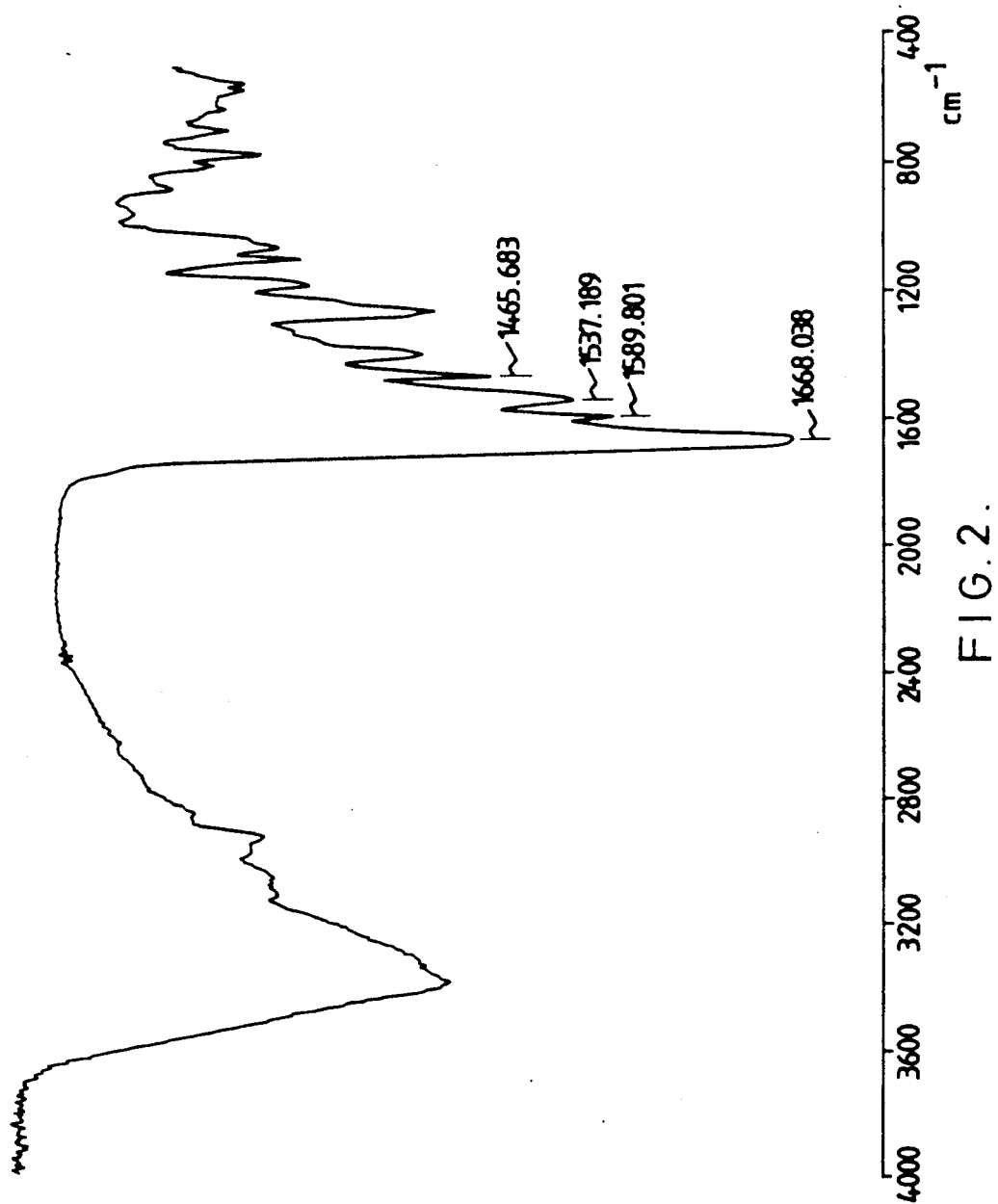
FIG. 2 shows the infrared absorption spectrum of mureidomycin E.
Figure 3:
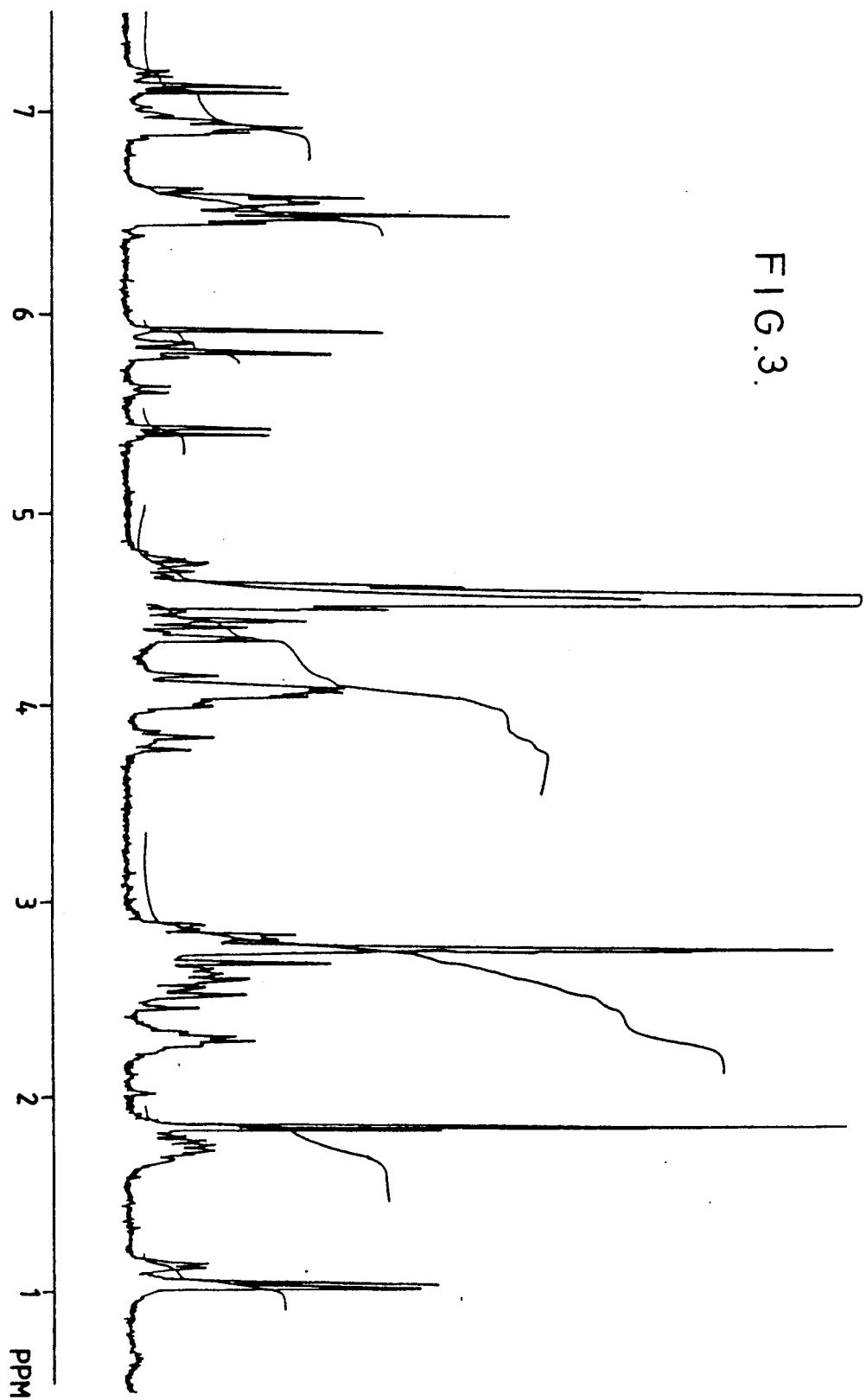
FIG. 3 shows the nuclear magnetic resonance spectrum of mureidomycin E.
Figure 4:
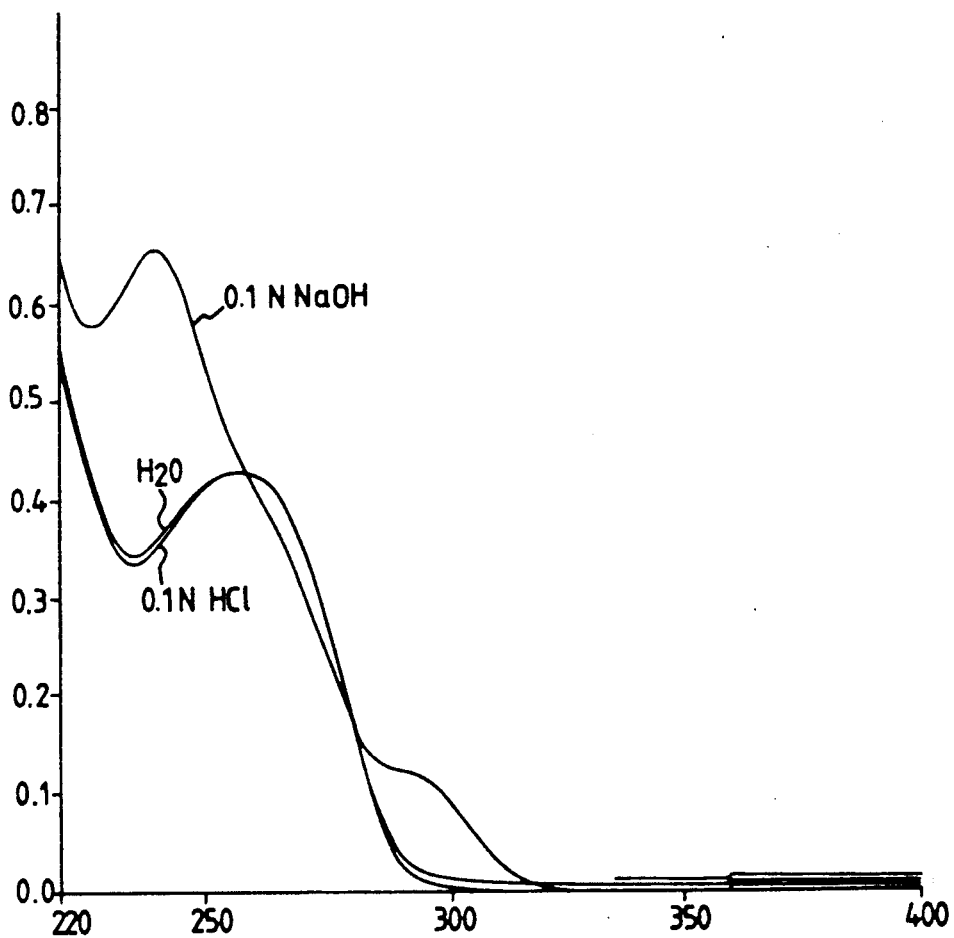
FIG. 4 shows the ultraviolet absorption spectrum of mureidomycin F.
Figure 5:
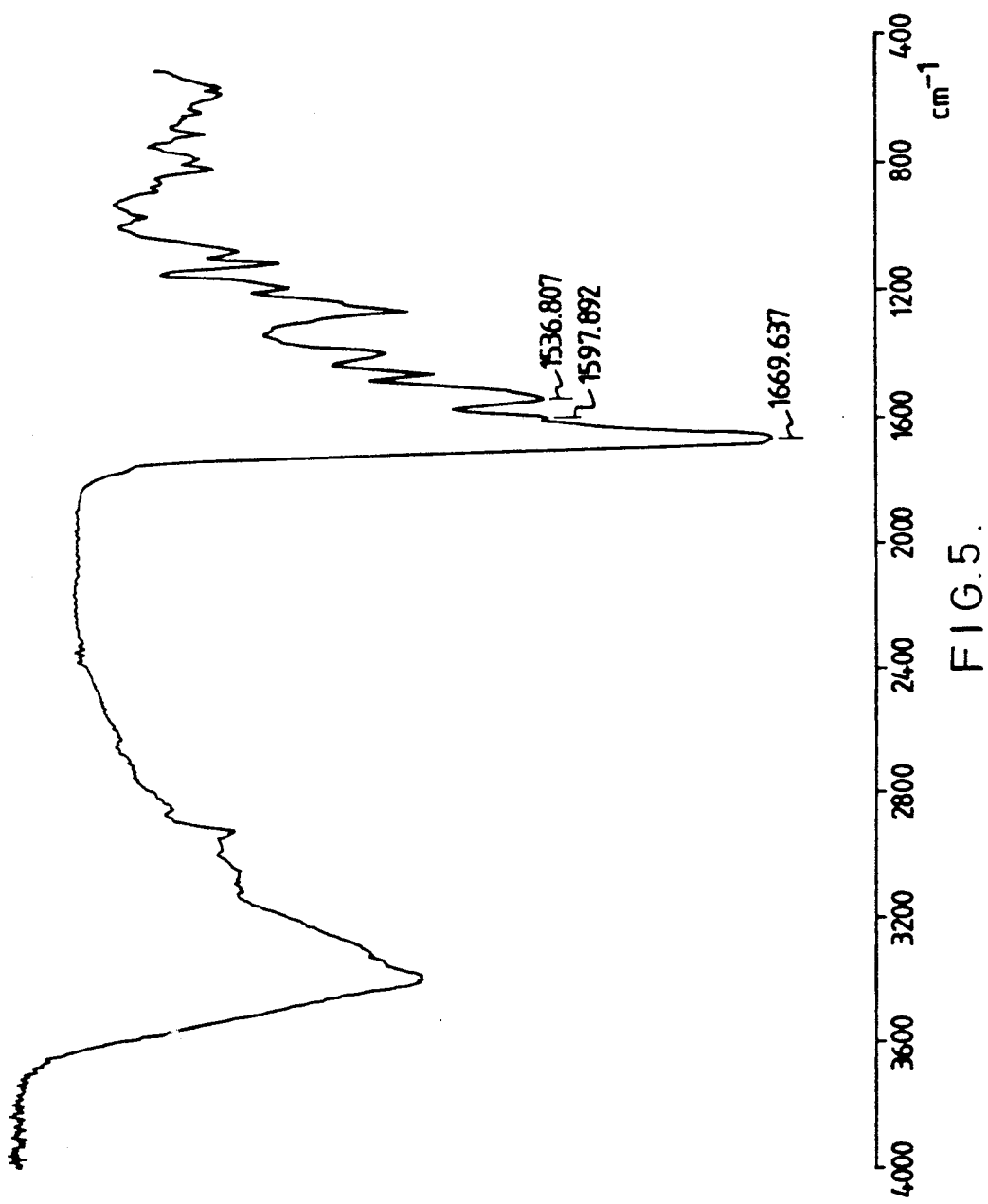
FIG. 5 shows the infrared absorption spectrum of mureidomycin F.
Figure 6:
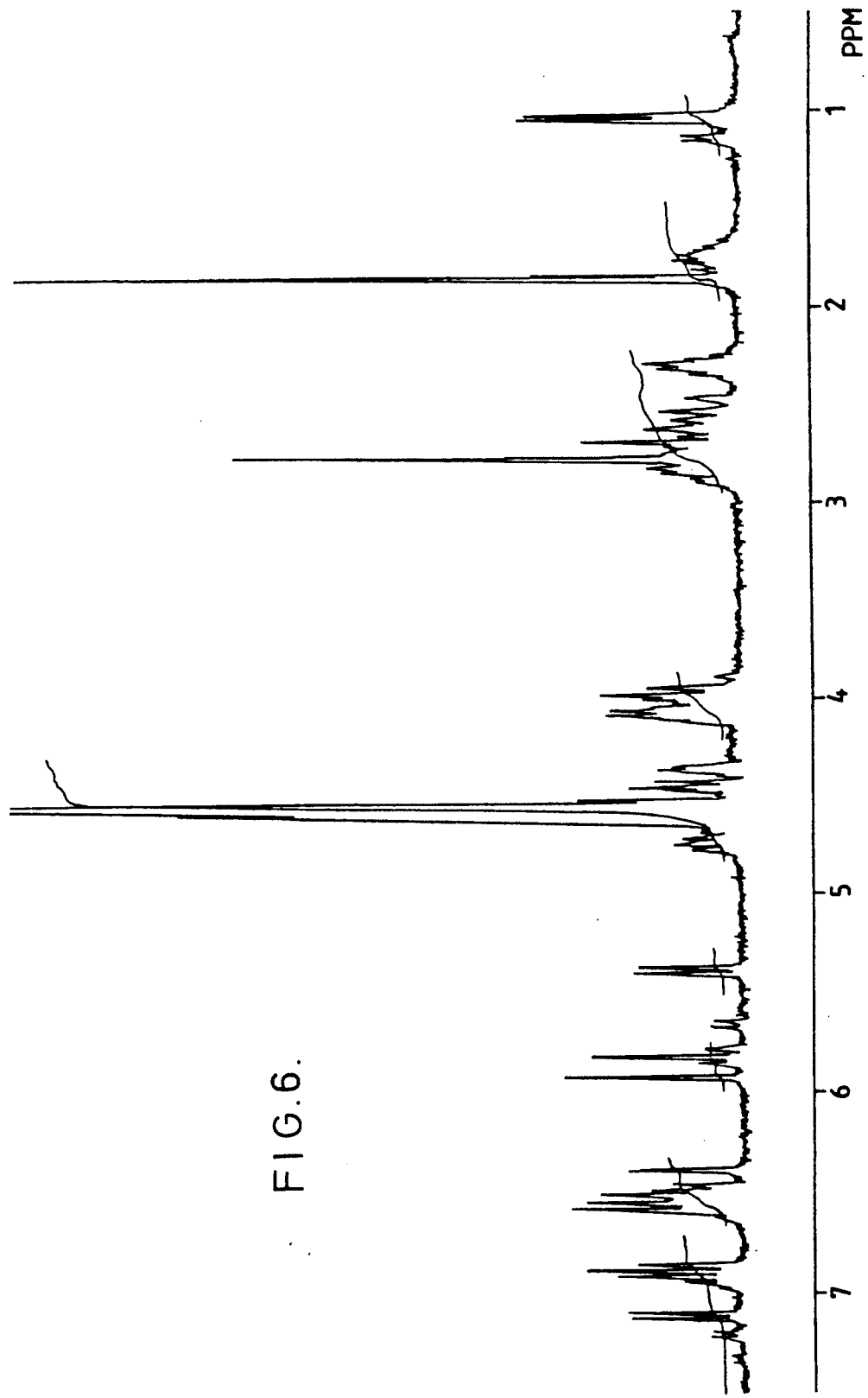
FIG. 6 shows the nuclear magnetic resonance spectrum of mureidomycin F.

Mureidomycin E has the following physico-chemical properties:

1) Character and appearance: Amphoteric soluble in water, white powder;
2) Specific rotation: $[\alpha_D^{25} -34.2°$ (c 1.17, 50% v/v aqueous methanol);
3) Elemental analysis: C, 48.57%; H, 5.35%; N, 11.34%; S, 3.00%—measured as the hydrate;
4) Molecular weight; 852 [high resolution mass spectrum FAB MS: 853.3212 (QM+)] (FAB MS is Fast Atom Bombardment Mass Spectroscopy);
5) Molecular formula: $C_{39}H_{48}N_8O_{12}S$;
6) Products resulting from acid hydrolysis: uracil; m-tyrosine; 2-amino-3-N-methylaminobutyric acid; 8-hydroxy-1,2,3,4-tetrahydro-3-isoquinoline carboxylic acid;
7) Ultraviolet absorption spectrum, $\lambda_{max}$nm ($E_{1\ cm}^{1\%}$); 258 nm (252) in neutral water; 258 nm (247) in 0.01N aqueous hydrochloric acid; 240 nm (432). 265 nm (235. shoulder) and 295 nm (80, shoulder) in 0.01N aqueous sodium hydroxide; the spectra are shown in FIG. 1 of the accompanying drawings;
8) Infrared absorption spectrum (KBr) $\nu_{max}$ cm$^{-1}$: the spectrum measured in a KBr disk is shown in FIG. 2 of the accompanying drawings;
9) Nuclear magnetic resonance spectrum, $\delta$ ppm: the spectrum (270 MHz) was measured in deuterium oxide using tetramethylsilane as external standard and is shown in FIG. 3 of the accompanying drawings (including conformational isomer);
10) Solubility: Soluble in water and methanol, slightly soluble in acetone, and insoluble in ethyl acetate, chloroform and benzene;
11) Color reactions: positive to ninhydrin, sulfuric acid, iodine, ferric chloride and Baeyer reactions;
12) Thin-layer chromatography: Rf value: 0.39; Adsorbent: Silica gel plate (Merck, Kieselgel 60 $F_{254}$) Developing solvent: a 4:2:1 by volume mixture of butanol, propanol and water;
13) High performance liquid chromatography: Column; Aquasil SS 372-N (Senshu Kagaku Co.); Developing solvent: a 200:100:100:40 by Volume mixture of chloroform, isopropanol, methanol and water; Flow rate; 1.0 ml/minute; Retention time: 4.7 minutes Mureidomycin F has the following physico-chemical properties:

1) Character and appearance: Amphoteric, soluble in water, white powder;
2) Specific rotation: $[\alpha_D^{25} -40.3°$ (c 1.05, 50% v/v aqueous methanol);
3) Elemental analysis: C, 50.40%; H, 5.53%; N, 11.20%; S, 2.92%—measured as the hydrate;
4) Molecular weight: 852 [high resolution mass spectrum FAB MS: 853.3180 (QM+)]
5) Molecular formula: $C_{39}H_{48}N_8O_{12}S$;
6) Products resulting from acid hydrolysis: uracil; m-tyrosine; 2-amino-3-N-methylaminobutyric acid; 6-hydroxy-1,2,3,4-tetrahydro-3-isoquinoline carboxylic acid;
7) Ultraviolet absorption spectrum. $\lambda_{max}$ nm ($E_{1\ cm}^{1\%}$): 258 nm (232) in neutral water; 258 nm (232) in 0.01N aqueous hydrochloric acid: 240 nm (352), 265 nm (200, shoulder) and 295 nm (64, shoulder) in 0.01N aqueous sodium hydroxide; the spectra are shown in FIG. 4 of the accompanying drawings;
8) Infrared absorption spectrum (KBr) $\nu_{max}$ cm$^{-1}$: the spectrum measured in a KBr disk is shown in FIG. 5 of the accompanying drawings;
9) Nuclear magnetic resonance spectrum, $\delta$ ppm: the spectrum (270 MHz) was measured in deuterium oxide using tetramethylsilane as external standard and is shown in FIG. 6 of the accompanying drawings (including conformational isomer);
10) Solubility: Soluble in water and methanol, slightly soluble in acetone, and insoluble in ethyl acetate, chloroform and benzene;
11) Color reactions: Positive to ninhydrin, sulfuric acid, iodine, ferric chloride and Baeyer reactions;
12) Thin-layer chromatography: Rf value; 0.34; Adsorbent: Silica gel plate (Merck, Kieselgel 60 $F_{254}$); Developing solvent; a 4:2:1 by volume mixture of butanol, propanol and water;
13) High performance liquid chromatography: Column: Aquasil SS 372-N (Senshu Kagaku Co.); Developing solvent: a 200:100:100:40 by volume mixture of chloroform, isopropanol, methanol and water; Flow rate; 1.0 ml/minute; Retention time; 5.3 minutes.

Mureidomycins E and F and their derivatives as well as their salts and esters, represented by the above general formula (1), can alternatively be obtained by reacting mureidomycin A, having the formula:

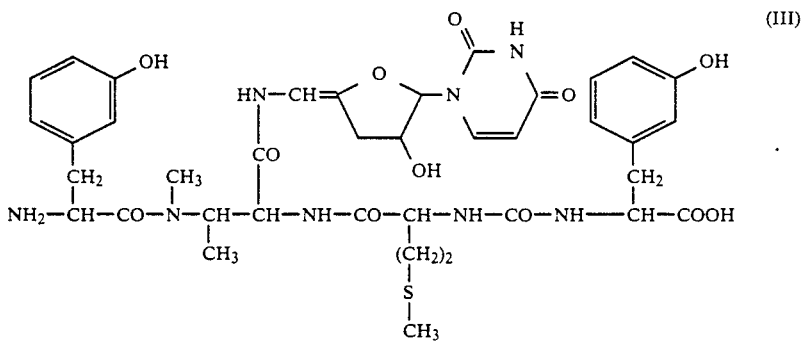

or a salt or ester thereof, with an aldehyde of the formula:

R—CHO  (IV)

(wherein R is as defined above) and optionally salifying, desalifying or esterifying the compound thus obtained.

This preparation can be carried out by reacting about one mole of mureidomycin A or salt or ester thereof with about 3 to 6 moles of aldehyde of the above formula (IV). The reaction is preferably performed in an inert solvent. There are no specific limitations on the choice of solvent, provided that it does not interfere with the course of the reaction, and suitable examples include water, ethers such as tetrahydrofuran and dioxane, and mixtures of water with such organic solvents. The reaction temperature will usually be in the range of 5°–100° C., and preferably between room temperature and 80° C. The reaction time will depend on the nature of the reactants and the temperature employed, but will usually be in the range of from 1 to 24 hours.

On completion of the reaction, the desired product may be isolated and purified by the same techniques as already mentioned above for the product obtained by the microbial fermentation route. If desired the product can also be salified, desalified or esterified, as already described above.

Mureidomycin A, used as starting material in the above reaction, can be obtained by cultivation of the same *Streptomyces flavidovirens* SANK 60486 as is used in the present invention for the production of mureidomycins E and F, and its production isolation and purification are more fully described in our aforementioned U.S. patent application Ser. No. 51,665 filed on May 18, 1987.

Figure 7B:
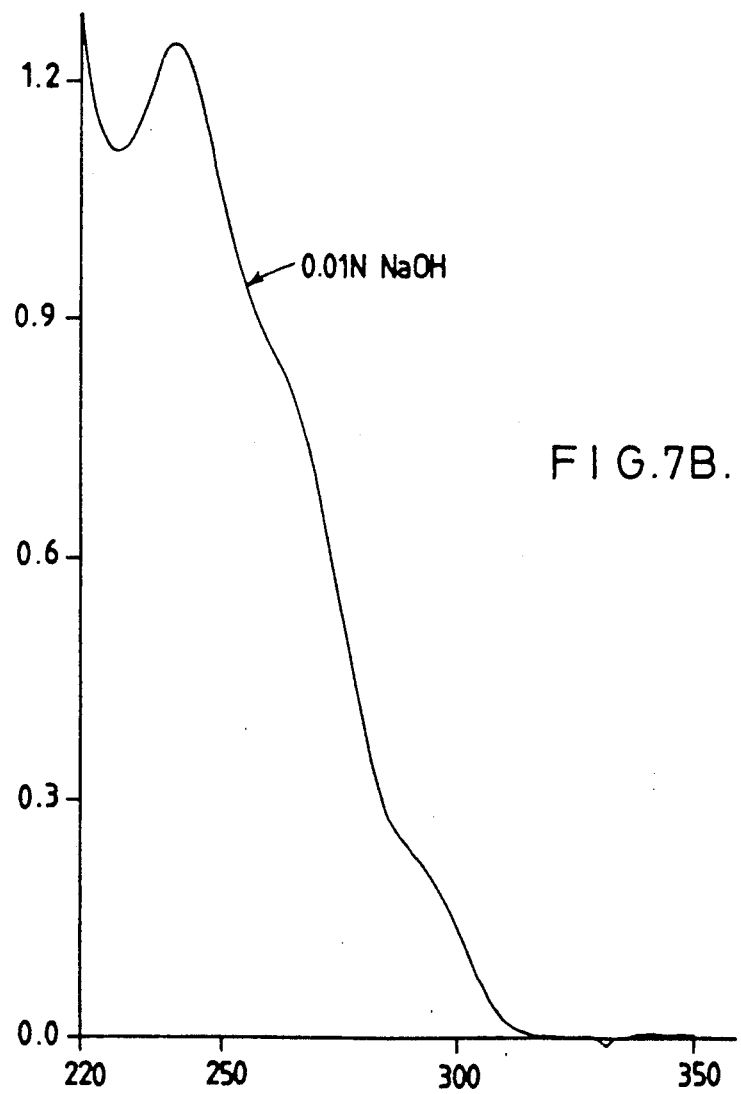
Figure 8:
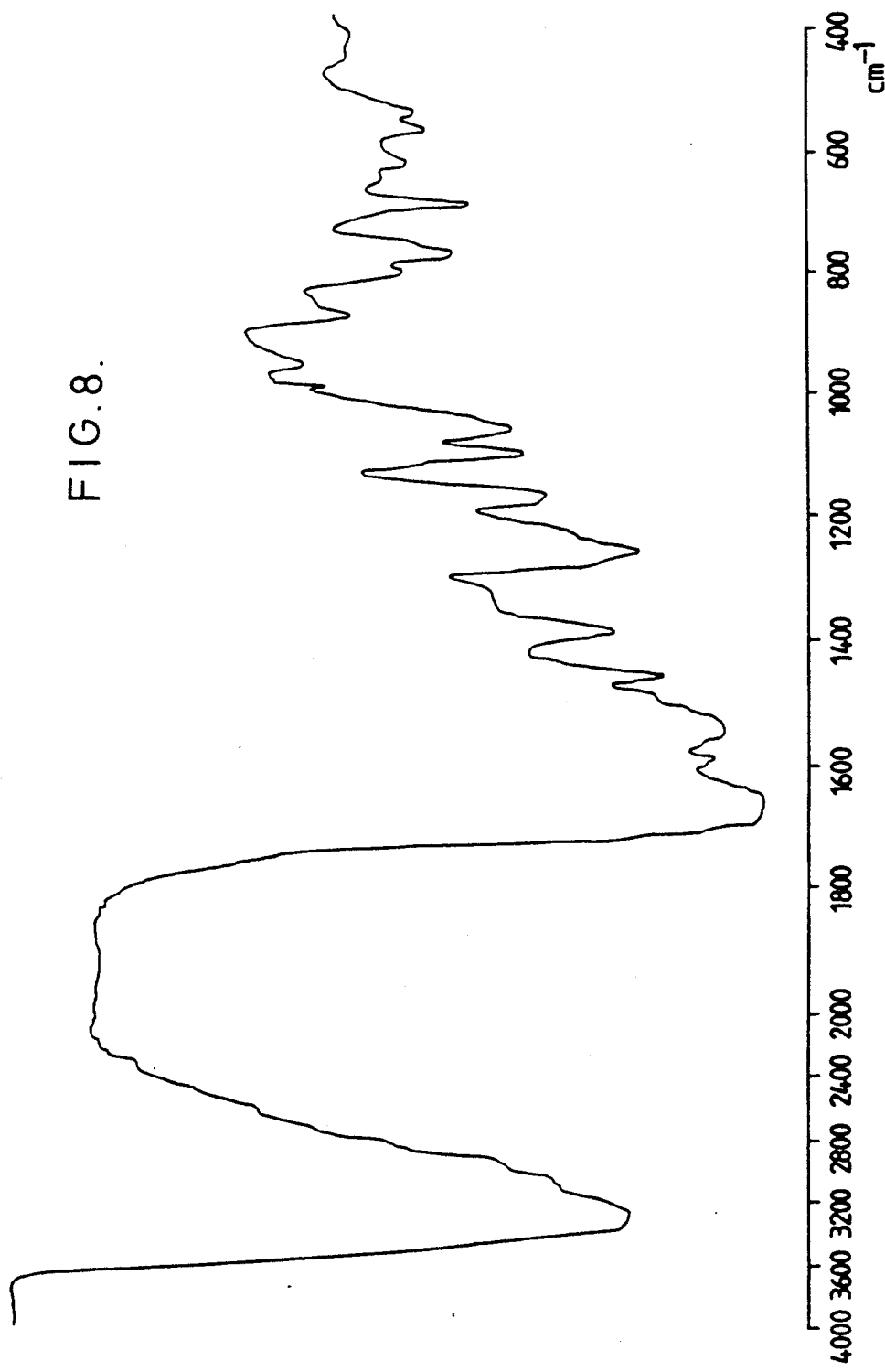
FIG. 8 shows the infrared absorption spectrum of mureidomycin A.
Figure 9:
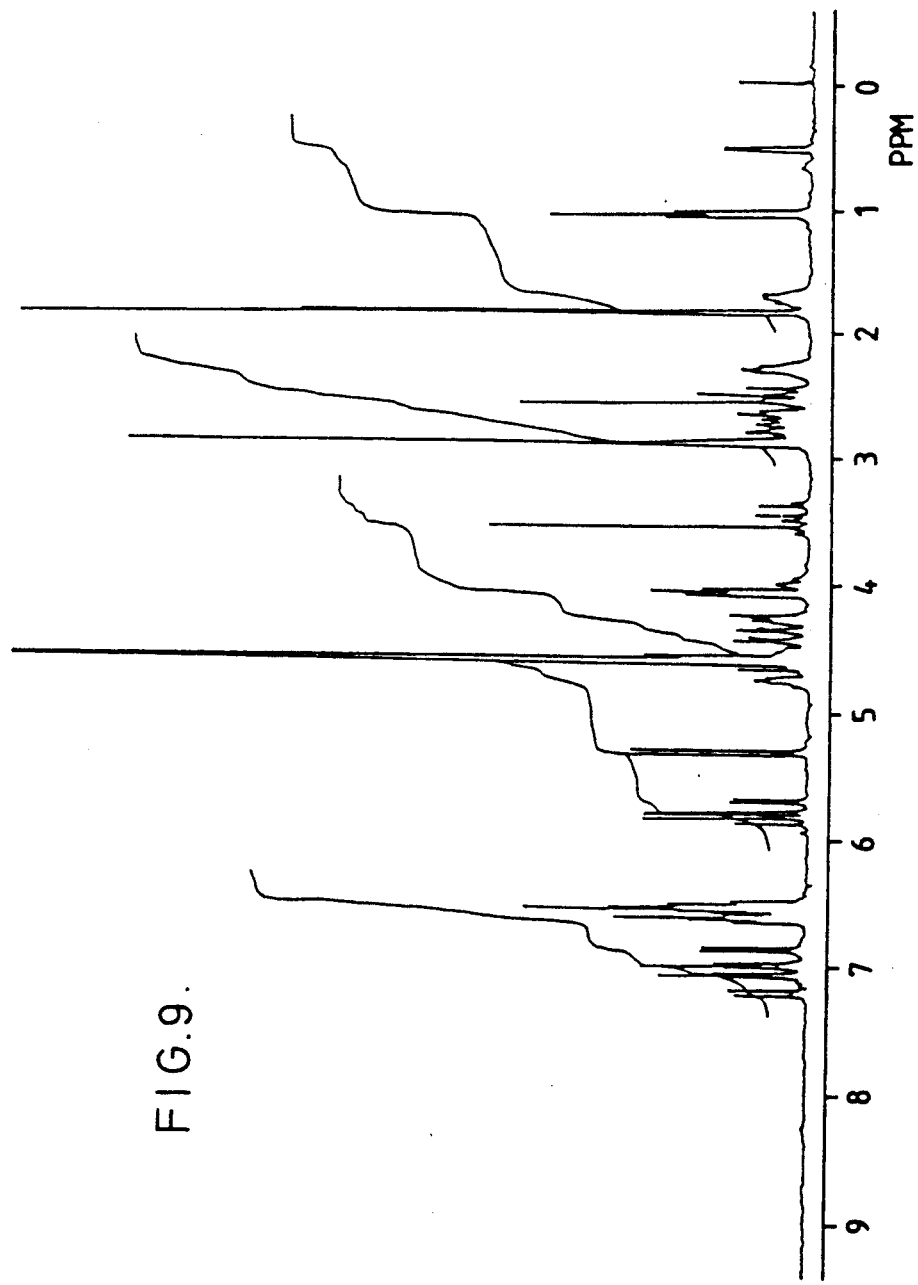
FIG. 9 shows the nuclear magnetic resonance spectrum of mureidomycin A.

Mureidomycin A has the following physico-chemical properties:

1) Character and appearance; Amphoteric, soluble in water, white powder;
2) Specific rotation: $[\alpha]_D^{25}$ +40.9° (c 0.69, 50% v/v aqueous methanol);
3) Elemental analysis: C, 49.73%: H, 5.65%; N, 12.08%; S, 3.40%—measured as the hydrate;
4) Molecular weight: 840 [high resolution mass spectrum FAB MS: 841.31798 (QM+)] (FAB MS is Fast Atom Bombardment Mass Spectroscopy);
5) Molecular formula: $C_{38}H_{48}N_8O_{12}S$;
6) Products resulting from acid hydrolysis: uracil; m-tyrosine; 2-amino-3-N-methylaminobutyric acid;
7) Ultraviolet absorption spectrum, $\lambda_{max}$ nm ($E_{1\ cm}^{1\%}$): 260 nm (348) in neutral water; 258 nm (358) in 0.01N aqueous hydrochloric acid; 240 nm (499), 265 nm (330, shoulder) and 295 nm (78, shoulder) in 0.01N aqueous sodium hydroxide; the spectra are shown in FIGS. 7A and 7B of the accompanying drawings;
8) Infrared absorption spectrum (KBr) $\nu_{max}$ cm$^{-1}$; the spectrum measured in a KBr disk is shown in FIG. 8 of the accompanying drawings;
9) Nuclear magnetic resonance spectrum, δ ppm: the spectrum (400 MHz) was measured in dimethyl sulfoxide using tetramethylsilane as external standard and is shown in FIG. 9 of the accompanying drawings (including conformational isomer);
10) Solubility: Soluble in water and methanol, slightly soluble in acetone, and insoluble in ethyl acetate, chloroform and benzene;
11) Color reactions: Positive to ninhydrin sulfuric acid, iodine, ferric chloride and Baeyer reactions;
12) Thin-layer chromatography: Rf value; 0.36; Adsorbent: Silica gel plate (Merck, Kieselgel 60 F$_{254}$); Developing solvent: a 4:2:1 by volume mixture of butanol, propanol and water;
13) High performance liquid chromatography: Column: Aquasil SS 372-N (Senshu Kagaku Co.); Developing solvent; a 200:100:100:40 by volume mixture of chloroform, isopropanol, methanol and water; Flow rate: 1.0 ml/minute; Retention time: 3.92 minutes.

The minimal inhibitory concentrations (MIC) of mureidomycins E and F against various Gram-positive and Gram-negative bacteria were determined by the agar dilution method, using a Mueller-Hinton agar medium (produced by Difco). The results are shown in Table 4.

TABLE 4

| | | MIC (μg/ml) | |
|---|---|---|---|
| | | Mureidomycin E | Mureidomycin F |
| *Staphylococcus aureus* | FDA 209P JC-1 | >200 | >200 |
| *Escherichia coli* | NIHJ JC-2 | >200 | >200 |
| *Proteus mirabilis* | SANK 70461 | >200 | >200 |
| *Pseudomonas aeruginosa* | SANK 75775 | 6.25 | 25 |
| *Pseudomonas aeruginosa* | SANK 75175 | 25 | 50 |
| *Pseudomonas aeruginosa* | SANK 70970 | 25 | 100 |
| *Pseudomonas aeruginosa* | NRRL B1000 | 25 | 3.13 |
| *Pseudomonas aeruginosa* | ATCC 13388 | 25 | 3.13 |
| *Pseudomonas aeruginosa* | SANK 70579 | <0.4 | 1.56 |
| *Pseudomonas aeruginosa* | NCTC 10490 | <0.4 | 0.8 |
| *Serratia marcescens* | SANK 73060 | >200 | >200 |

Tests also show that methylmureidomycins E and F and phenylmureidomycins E and F inhibit the growth of *Pseudomonas aeruginosa* SANK 70579.

From the above data, mureidomycins E, F and their derivatives are seen to be active against Gram-negative bacteria, particularly against bacteria of the genus Pseudomonas.

No toxicity was observed in mice receiving intravenously 400 mg/kg of mureidomycin E or F or one of their derivatives.

From the above findings, it can be seen that mureidomycins E and F and their derivatives can be used as antibiotics against various diseases caused by bacterial infections. The route of administration can vary widely and may be parenteral (e.g. by subcutaneous, intravenous or intramuscular injection or by suppository) or oral (in which case it may be administered in the form of a tablet, capsule, powder or granule). The dose will, of course, vary with the nature of the disease to be treated, the age, condition and body weight of the patient and the route and time of administration; however, for an adult human patient, a daily dose of from 0.1 to 10 grams is preferred and this may be administered in a single dose or in divided doses.

Mureidomycins AP, BP, CP, DP, EP and FP of the above formula (II) and their salts can be prepared by hydrolysis of the corresponding mureidomycin A, B, C, D, E or F of formula (A) above, or a salt thereof, optionally followed by salification or desalification of the product thus obtained, when appropriate. The hydrolysis can be effected by treating the starting material with a suitable acid, base or protease, optionally in the presence of a solvent.

Acids, bases and proteases conventionally employed in previously known similar hydrolysis reactions may be used for this preparation, without particular limitation. For example, there can be used a mineral acid such as hydrochloric, sulfuric or hydrobromic acid; or an alkali or alkaline earth metal hydroxide or carbonate such as sodium hydroxide, potassium hydroxide, barium hydroxide, sodium carbonate, potassium carbonate or calcium carbonate; but it is preferred to use a protease such as pepsin, cathepsin, pronase or chymotrypsin, and particularly pepsin. It is also preferred to carry out the hydrolysis in the presence of a solvent, so that it will proceed more smoothly. There is no particular limitation on the choice of the solvent, provided that it has no adverse effect on the reaction, and suitable examples include water, aqueous methanol, and mixtures of an alcohol such as methanol or ethanol with an ether such as tetrahydrofuran or dioxane or a sulfoxide such as dimethyl sulfoxide. If the hydrolysis is effected with an acid or a base, the reaction temperature is not particularly critical, and for instance the reaction may be performed at room temperature or at the reflux temperature of the solvent (if one is employed). On the other hand, if the hydrolysis is effected with a protease, then conventional enzymatic reaction conditions should be employed; for example, in the case of pepsin the reaction may be carried out in a reaction solvent adjusted to pH 2.5 with dilute hydrochloric acid, at a temperature from 10° to 60° C. and more preferably around 37° C. for a period of from 10 hours to 3 days.

After completion of the reaction, the desired compound can be isolated and purified by conventional techniques, utilizing its physico-chemical properties. (The physico-chemical properties for mureidomycins AP, BP, CP, DP, EP and FP are set out below, in Examples 9 to 14, respectively). For example, suitable methods include: extraction with solvents; ion-exchange through resins, for example, anion exchange resins such as Dowex SBR-P (Dow Chemical Co.) or cation exchange resins such as Dowex 50 W (Dow Chemical Co.) or IRC-50, CG-50 (Rohm & Haas Co.); chromatography through active carbon as the absorbent or through non-ionic absorption resins such as Amberlite XAD-2, XAD-4 or XAD-7 (Rohm and Hass Co.) or Diaion HP 10, HP 20, CHP 20P or HP 50 (Mitsubishi Chemical Industries, Ltd.); and chromatography through silica gel or alumina. Furthermore, separation, collection and purification of the metabolites may be performed by using any one or more of the following operations, which may be combined in any order or repeated, if desired: partition column chromatography over cellulose such as Avicel (Asahi Chemical Industry Co., Ltd.) or Sephadex LH-20 (pharmacia Co.); gel filtration using Sephadex G-10, G-25, G-50 or G-100 (Pharmacia Co.) or Toyopearl HW-40 (Toyo Soda Manufacturing Co., Ltd.); crystallization; and recrystallization. ("Dowex", "Amberlite", "Diaion", "Avicel", "Sephadex" and "Toyopearl" are all trade marks.)

Where the mureidomycin AP, BP, CP, DP, EP or FP is isolated in the form of a salt it may be converted to the free unsalified compound by conventional means, such as the use of ion-exchange resins or of adsorbents for reverse phase chromatography. Equally, the free unsalified compound may be salified by conventional means, for instance by treatment with an appropiate acid, such as one of those listed above, or with an appropiate base (e.g. a metal hydroxide or carbonate, such as sodium or potassium hydroxide, or sodium or calcium carbonate).

The production, isolation, purification and properties of mureidomycins A to D, used as starting materials for the preparation of mureidomycins AP to DP in the above reaction are described in our aforementioned U.S. patent application Ser. No. 51,665 filed on May 18, 1987, which has been replaced by continuation-in-part application Ser. No. 07/253,450 filed Oct. 4, 1988.

Mureidomycins AP to FP can be used as starting materials for the chemical synthesis of other mureidomycins, using per se conventional reaction steps. By way of example, the procedure described below and shown schematically in Reaction Scheme 1 can be used to synthesise mureidomycin C from mureidomycin AP.

Dicyclohexylcarbodiimide (DCC) is added with stirring and under ice-cooling to a solution of N-carbobenzoxyglycine (CBZ-glycine), and a solution of mureidomycin AP is added dropwise to the resulting mixture. The reaction is allowed to proceed under ice-cooling for about 3 to 4 hours. After filtration, the solvent is removed by distillation and the residue is purified by a conventional method, e.g. liquid chromatography or TLC to give a glycine derivative having the formula (V) in Reaction Scheme 1. A ureido derivative having the formula (VI) is prepared from methionine and m-tyrosine by a conventional method, and dissolved in a suitable organic solvent. DCC is added to this solution with stirring and under ice-cooling, and then a solution of the glycine derivative (V) is added to the resulting mixture. The reaction is allowed to proceed under ice-cooling for about 3 to 4 hours. After filtration, the solvent is removed by distillation. (In all of the preceding steps, any suitable organic solvent, such as ethyl acetate or acetonitrile, may be used for making up the solutions).

The resultant residue is dissolved in a suitable organic solvent (e.g. 80% aqueous methanol) and subjected to catalytic reduction with a suitable catalyst (e.g. 10% palladium on carbon) for about 2 to 3 hours. After completion of the reduction, the catalyst is removed by filtration and the organic solvent is distilled off. The aqueous layer is freeze-dried to afford mureidomycin C in the form of a powder.

In the reaction scheme, "CBZ" stands for N-carbobenzoxy.

mark for a product of Johns-Manville Products Corp. New Jersey, U.S.A.) filter aid was added and the mixture was filtered, to give 30 liters of a filtrate. This filtrate was adsorbed on 3 liters of Amberlite XAD-2 in a chromatography column. The column was washed, in turn, with 15 liters of deionized water and then with 12 liters of water containing 15% V/V methanol, after which it was eluted with 15 liters of water containing 40% v/v methanol. The methanol was then removed from the fractions containing active components by distillation under reduced pressure, after which the residual solution was lyophilized, to give 17.4 g of a crude product as a powder.

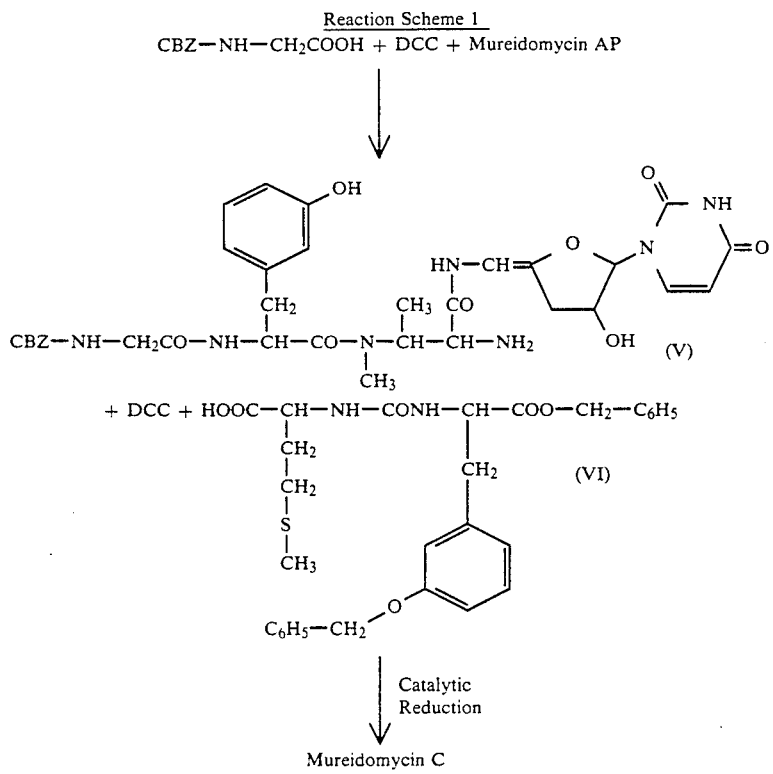

The invention is further illustrated by the following Examples.

EXAMPLE 1

Mureidomycins E, F and A by fermentation

One platinum loopful growth of *Streptomyces flavidovirens* SANK 60486 was inoculated into a 500 ml Erlenmeyer flask containing 80 ml of medium A, which has the following composition (percentages are by weight):

| MEDIUM A | |
|---|---|
| Glucose | 3% |
| Pressed yeast | 1% |
| Soybean meal | 3% |
| Calcium carbonate | 0.4% |
| Magnesium sulfate heptahydrate | 0.2% |
| Anti-foaming agent (Nissan Disfoam CB-442) | 0.01% |
| Water | the balance |
| (pH 7.2 before sterilization) | |

The microorganism was then cultured for 84 hours at 22° C., using a rotary shaker at 220 r.p.m.

25 ml of the resulting seed culture were inoculated into each of four 2-liter Erlenmeyer flasks, each containing above. The microorganism was then cultured at 22° C. for 24 hours, using a rotary shaker at 220 r.p.m. The resulting cultured broths were combined. 750 ml of this broth were then inoculated into each of two 30 liter jar fermentors, each containing 15 liters of medium A, and the microorganism was then cultured at 22° C. for 96 hours, whilst aerating at the rate of 15 liters per minute and agitating at 150 r.p.m.

At the end of this time, the two batches of cultured broth were combined. Celite 545 (a registered trade 17 g of this crude powder were dissolved in 3 liters of deionized water, and the solution was passed through a column containing 800 ml of Amberlite CG-50 (H+), to adsorb the active component. The active component was eluted from the column with 0.5M aqueous ammonia. The eluted active fractions (4 liters) were collected and concentrated to a volume of 1.0 liter by evaporation under reduced pressure. The concentrate (1.0 liter) was passed through 500 ml of DE-52 ion exchanger (Whatman Ltd.), which had been pre-equilibrated with a 0.1M aqueous solution of ammonium bicarbonate and the active component was adsorbed on the column. The column was eluted with 0.2M aqueous ammonium bicarbonate. The fractions (1 liter) containing the active component were collected and adsorbed on a column containing 200 ml of Diaion HP 20 (Mitsubishi Chemical Industries, Ltd.), after which the column was eluted with 500 ml of 50% v/v aqueous acetone, to give an active component. The fractions containing the active component were concentrated, by evaporation under reduced pressure and lyophilized to afford 15 g of a crude powdery product containing mureidomycins E, F and A.

14 g of this crude powder was dissolved in 500 ml of deionized water, and the active component was adsorbed on a column containing 500 ml of DE-52, which had been pre-equilibrated with 0.05 M aqueous ammonium bicarbonate. The column was washed with 0.05M aqueous ammonium bicarbonate, and then eluted with 0.1M aqueous ammonium bicarbonate, to give fractions, each containing 20 ml of the eluent. Fractions 80 to 130 containing the active components were collected and adsorbed on a column containing HP 20, in order to deionize them. The deionized eluent was concentrated by evaporation under reduced pressure, and the residue was lyophilized to afford 3.1 g of a partially purified powder.

3.0 g of this partially purified powder were subjected to column chromatograpy through a column containing 100 g of silica gel, which was eluted with a mixture of butanol, propanol and water (8:4:1) to give fractions each containing 20 ml of the eluent. Fractions 13 to 70 were collected, mixed with water, concentrated under reduced pressure and lyophilized, to give 320 mg of crude powdery product containing antibiotics mureidomycins E, F and A.

A solution of 300 mg of the crude powder thus obtained dissolved in 30% v/v aqueous methanol was adsorbed on a column containing 1000 ml of Toyopearl HW-40, and the column was eluted with 30% v/v aqueous methanol to give fractions, each containing 10 ml of the eluent. Fractions 95 to 105 were collected as active fractions, and these were adsorbed on a column containing 10 ml of Amberlite CG-50 (H+ type), which was then eluted with 0.5M aqueous ammonia. The fractions containing active components were collected, concentrated by evaporation under reduced pressure and lyophilized, to afford 15 mg of mureidomycin E having the physico-chemical properties set out above.

Eluent fractions 80 to 90 and 50 to 70, respectively, were similarly worked up, to afford 32 mg of mureidomycin F and 24 mg of mureidomycin A, each having the respective physico-chemical properties set out above.

EXAMPLE 2

Mureidomycins E and F from mureidomycin A 270 mg of mureidomycin A were dissolved in 60 ml of deionized water, 300 μl of 30% aqueous formaldehyde were added to the solution, and the resulting mixture was allowed to stand overnight in order to complete the reaction.

The reaction mixture was then adsorbed onto a 1500 ml Toyopearl column, which was eluted with 30% aqueous methanol, to give fractions each containing 15 ml of eluent. Fractions 81 to 88 containing active components were collected, concentrated by evaporation under reduced pressure, and lyophilized to give 65 mg of mureidomycin F having the physico-chemical properties set out above.

Fractions 92 to 100 were similarly worked up to give 64 mg of mureidomycin E having the physico-chemical properties set out above.

EXAMPLE 3

Methylmureidomycins E and F from mureidomycin A 200 mg of mureidomycin A were dissolved in 50 ml of deionized water, 500 μl of acetaldehyde were added to the solution, and the resulting mixture was kept stirred at 70° C. for 3 hours to complete the reaction.

The reaction mixture was then adsorbed onto a 1500 ml Toyopearl column, which was eluted with 30% aqueous methanol, to give fractions each containing 15 ml of eluent. Fractions 85 to 90 containing active components were collected, concentrated by evaporation under reduced pressure, and lyophilized to give 30 mg of methylmureidomycin F having the physico-chemical properties set out below.

Fractions 93 to 98 were similarly worked up to give 27 mg of methylmureidomycin E having the physico-chemical properties set out below.

Methylmureidomycin E

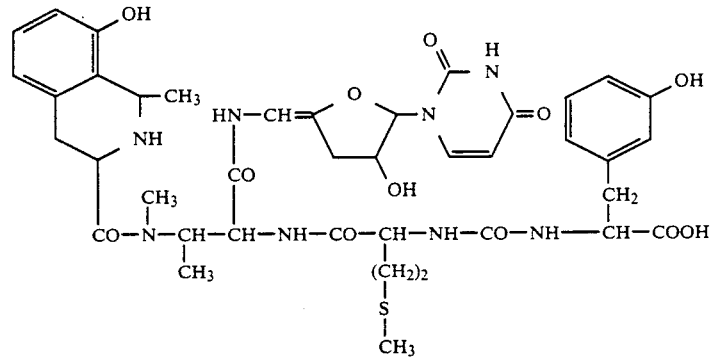

(VII)

Figure 10:
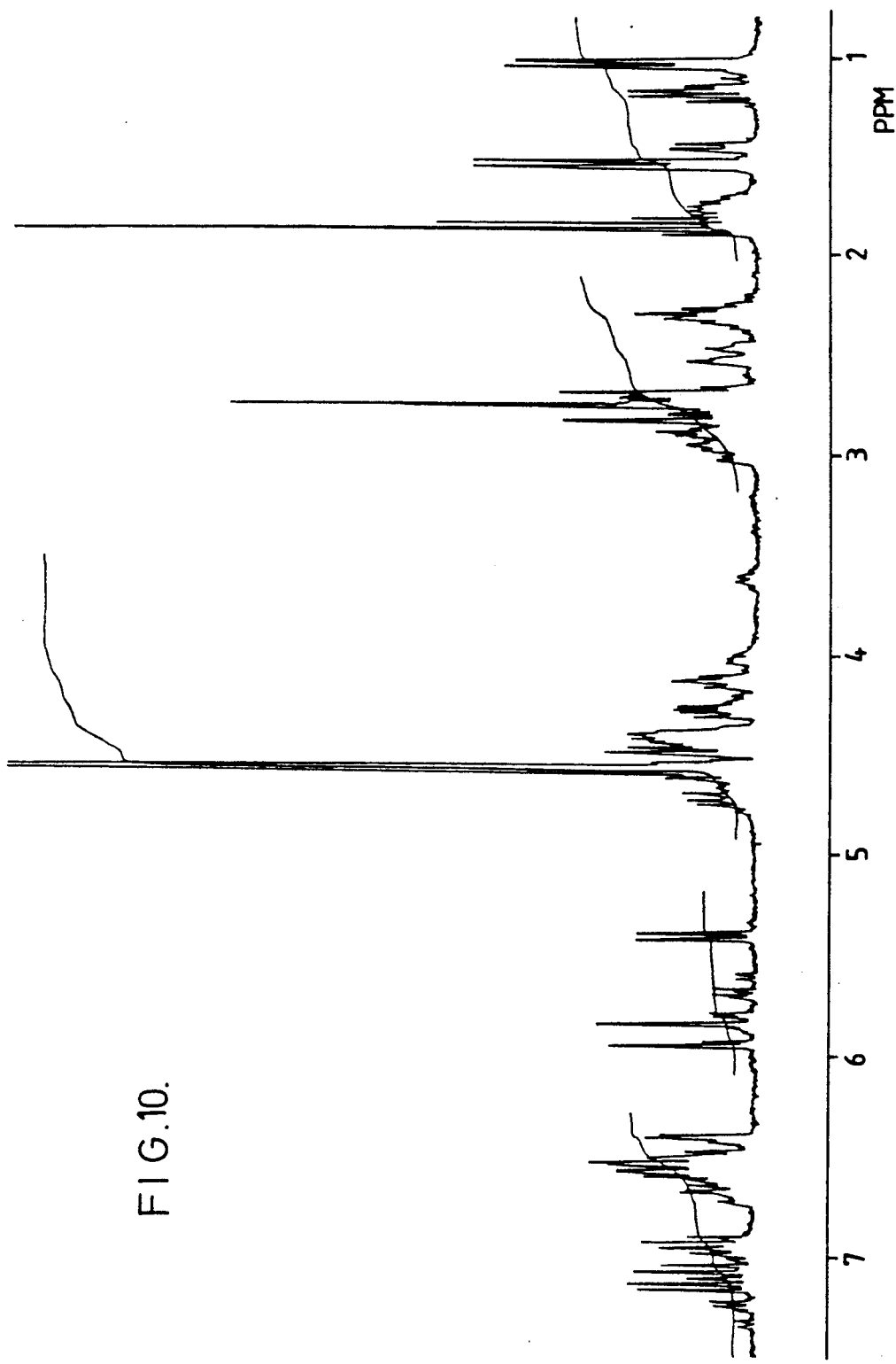
FIG. 10 shows the nuclear magnetic resonance spectrum of methylmureidomycin E.

1) Character and appearance: Amphoteric, soluble in water;
2) Molecular weight: 866;
3) Molecular formula: $C_{40}H_{50}N_8O_{12}S$;
4) Nuclear magnetic resonance spectrum, δ ppm: the spectrum (270 MHz) was measured in deuterium oxide using tetramethylsilane as external standard and is shown in FIG. 10 of the accompanying drawings (including conformational isomer):
5) Thin-layer chromatography; Rf value: 0.27; Adsorbent: Silica gel plate (Merck, Kieselgel 60 $F_{254}$); Developing solvent: a 4:2:1 by volume mixture of butanol, propanol and water;
6) High performance liquid chromatography: Column: Aguasil SS 372-N (Senshu Kagaku Co.); Developing solvent: a 200:100:100:40 by volume mixture of chloroform, isopropanol, methanol and water; Flow rate; 1.0 ml/minute; Retention time: 4.5 minutes.

Methylmureidomycin F

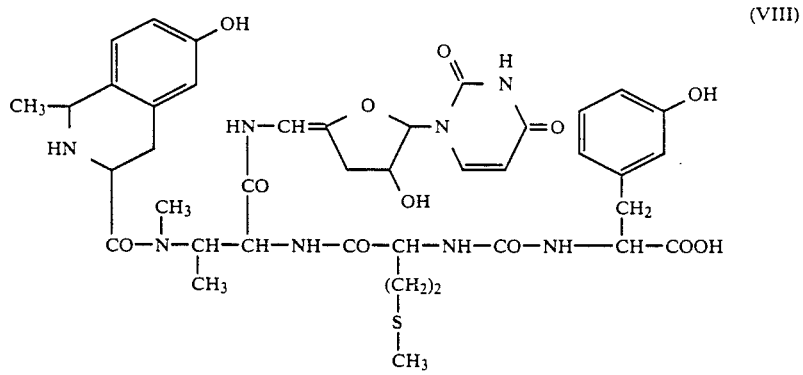

(VIII)

Figure 11:
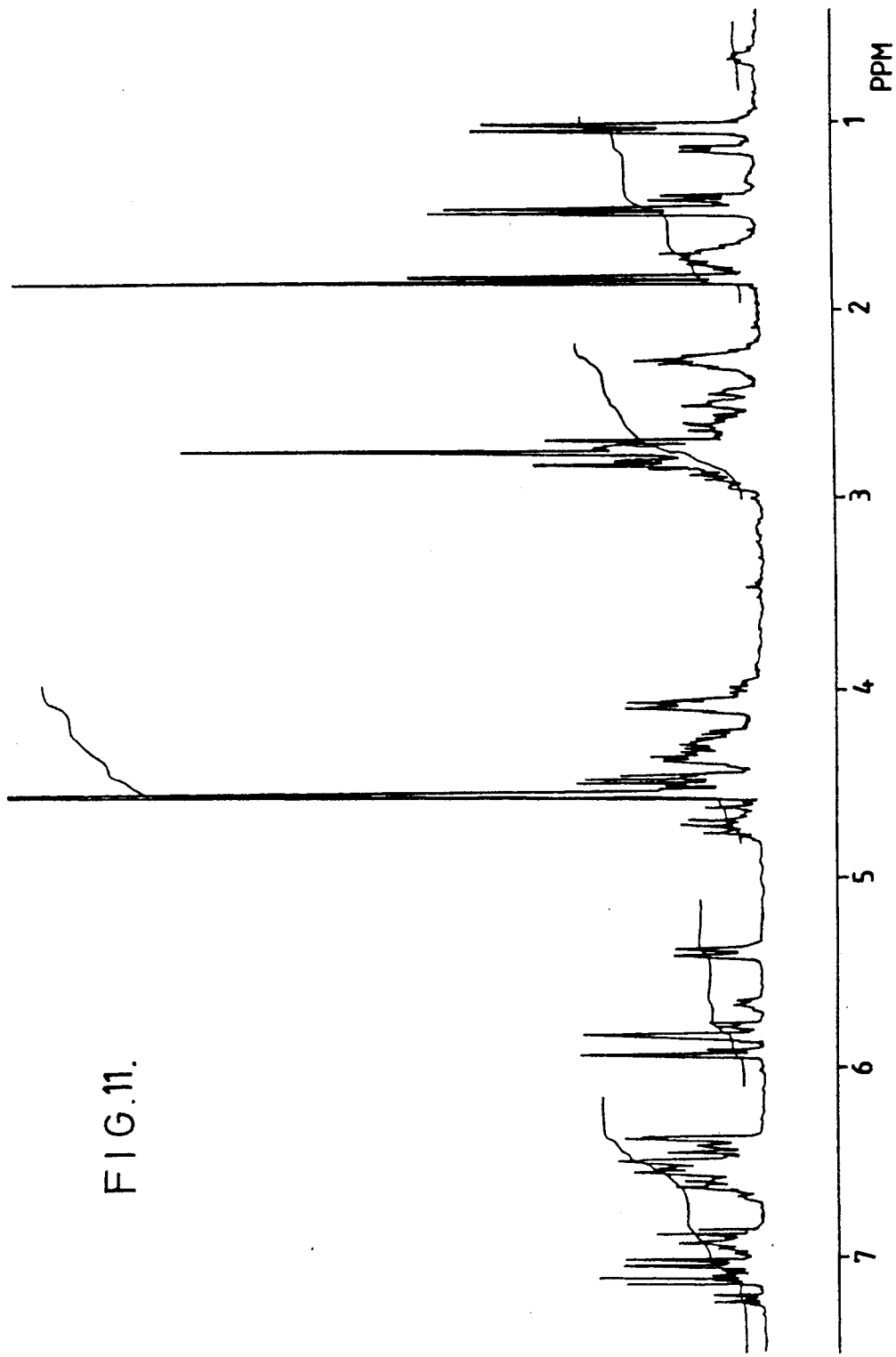
FIG. 11 shows the nuclear magnetic resonance spectrum of methylmureidomycin F.

1) Character and appearance: Amphoteric, soluble in water;
2) Molecular weight: 866;
3) Molecular formula: $C_{40}H_{50}N_8O_{12}S$;
4) Nuclear magnetic resonance spectrum, δ ppm: the spectrum (270 MHz) was measured in deuterium oxide using tetramethylsilane as external standard and is shown in FIG. 11 of the accompanying drawings (including conformational isomer);
5) Thin-layer chromatography: Rf value: 0.27; Adsorbent: Silica gel plate (Merck, Kieselgel 60 $F_{254}$); Developing solvent: a 4:2:1 by volume mixture of butanol, propanol and water;
6) High performance liquid chromatography: Column: Aquasil SS 372-N (Senshu Kagaku Co.); Developing solvent: a 200:100:100:40 by volume mixture of chloroform, isopropanol, methanol and water; Flow rate: 1.0 ml/minute., Retention time: 5.2 minutes.

EXAMPLE 4

Phenylmureidomycins E and F from mureidomycin A 200 mg of mureidomycin A were dissolved in 50 ml of deionized water, 500 μl of benzaldehyde were added to the solution, and the resulting mixture was kept stirred at 70° C. for 3 hours to complete the reaction.

The reaction mixture was then adsorbed onto a 1500 ml Toyopearl column, which was eluted with 30% aqueous methanol, to give fractions each containing 15 ml of eluent. Fractions 91 to 98 containing active components were collected, concentrated by evaporation under reduced pressure, and lyophilized to give 15 mg of phenylmureidomycin F having the physico-chemical properties set out below.

Fractions 101 to 106 were similarly worked up to give 8 mg of phenylmureidomycin E having the physico-chemical properties set out below.

Phenylmureidomycin E

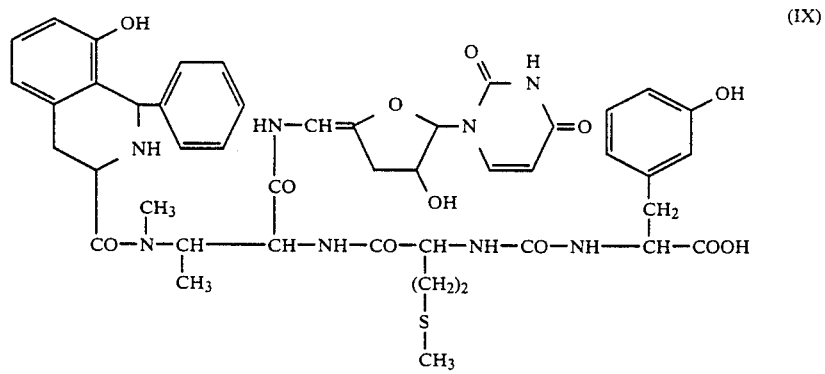

(IX)

1) Character and appearance: Amphoteric, soluble in water;
2) Molecular weight: 928;
3) Molecular formula; $C_{45}H_{52}N_8O_{12}S$;

Phenylmureidomycin F

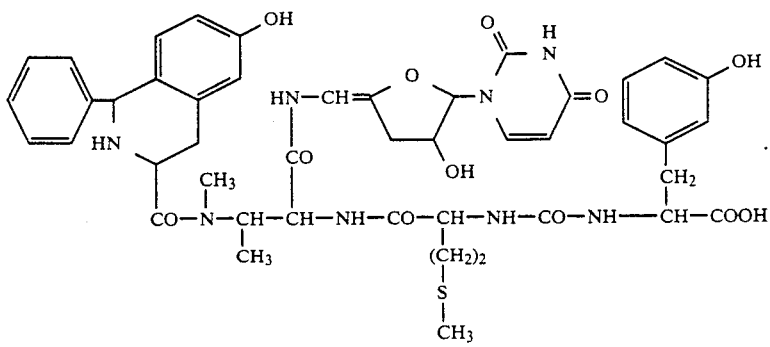

(X)

1) Character and appearance: Amphoteric, soluble in water;
2) Molecular weight: 928;
3) Molecular formula: $C_{45}H_{52}N_8O_{12}S$;

EXAMPLE 5

Mureidomycin E capsules for oral administration

The following powders were mixed:

| | |
|---|---|
| Mureidomycin E | 100 mg |
| Lactose | 100 mg |
| Maize starch | 148.5 mg |
| Magnesium stearate | 1.5 mg |
| TOTAL | 350 mg | and passed through a 30-mesh sieve (Tyler standard). The mixture (350 mg) was sealed into a gelatin capsule No. 2 to yield the desired capsule.

EXAMPLE 6

Mureidomycin F capsules for oral administration

The following powders were mixed:

| | |
|---|---|
| Mureidomycin F | 100 mg |
| Lactose | 100 mg |
| Maize starch | 148.5 mg |
| Magnesium stearate | 1.5 mg |
| TOTAL | 350 mg | and passed through a 30-mesh sieve (Tyler standard). The mixture (350 mg) was sealed into a gelatin capsule No. 2 to yield the desired capsule.

EXAMPLE 7

Mureidomycin E Injection 1.0 g of mureidomycin E was dissolved in 5.0 ml of a 1/15M phosphate buffer solution (pH 6.9) and the solution was sealed into a 5 ml ampoule. The ampoule was sterilized by a conventional procedure to yield the desired injectible liquid.

EXAMPLE 8

Mureidomycin F Injection 1.0 g of mureidomycin F was dissolved in 5.0 ml of a 1/15M phosphate buffer solution and the solution was sealed into a 5 ml ampoule. The ampoule was sterilized by a conventional procedure to yield the desired injectible liquid.

EXAMPLE 9

Mureidomycin AP from mureidomycin A

A solution of 100 mg of mureidomycin A in 50 ml of deionized water was adjusted to pH 2.5 with 1N aqueous hydrochloric acid, 200 mg of pepsin (Boehringer Mannheim Co.) were then added, and the mixture was kept stirred overnight at 37° C. to complete the reaction.

The reaction mixture was then adjusted to pH 5.0 with 1N aqueous sodium hydroxide and adsorbed onto a column of 70 ml of Diaion CHP 20P resin (Mitsubishi Chemical Industries, Ltd.). The column was eluted successively with 350 ml of deionized water and 210 ml of 0.1% aqueous trifluoroacetic acid. The eluate was concentrated and lyophylized to afford 34 mg of mureidomycin AP having the following physico-chemical properties:

1) Character and appearance: Amphoteric, colorless powder soluble in water;
2) Molecular weight: 502;
3) Molecular formula; $C_{23}H_{30}N_6O_7$;
4) Thin-layer chromatography: Rf value: 0.13; Adsorbent: Silica gel plate (Merck, Kieselgel 60 $F_{254}$); Developing solvent: a 4:1:2 by volume mixture of n-butanol, acetic acid and water;
5) High performance liquid chromatography:
 Column: ODS H2151(Senshu Kagaku Co.);
 Developing solvent: 5% acetonitrile—0.1% aqueous trifluoroacetic acid;
 Flow rate: 1.0 ml/minute;
 Retention time: 8.3 minutes.

EXAMPLE 10

Mureidomycin BP from mureidomycin B

The procedure described in Example 9 was repeated, but reacting 100 mg of mureidomycin B and 200 mg of pepsin for 24 hours, to give 15 mg of mureidomycin BP having the following physico-chemical properties:

1) Character and appearance: Amphoteric, colorless powder soluble in water;
2) Molecular weight: 504;
3) Molecular formula; $C_{23}H_{32}N_6O_7$;
4) Thin-layer chromatography: Rf value: 0.13; Adsorbent: Silica gel plate (Merck, Kiesegel 60 $F_{254}$); Developing solvent; a 4:1:2 by volume mixture of n-butanol, acetic acid and water;
5) High performance liquid chromatography;
 Column ODS H2151(Senshu Kagaku Co.);
 Developing solvent: 5% acetonitrile—0.1% aqueous trifluoroacetic acid;
 Flow rate: 1.0 ml/minute;

EXAMPLE 11

Mureidomycin CP from mureidomycin C

The procedure described in Example 9 was repeated, but reacting 100 mg of mureidomycin C and 200 mg of pepsin for 48 hours, to give 28 mg of mureidomycin CP having the following physico-chemical properties:
1) Character and appearance; Amphoteric, colorless powder soluble in water;
2) Molecular weight: 559;
3) Molecular formula: $C_{25}H_{33}N_7O_8$;
4) Thin-layer chromatography: Rf value: 0.13; Adsorbent: Silica gel plate (Merck, Kieselgel 60 $F_{254}$); Developing solvent: a 4:1:2 by volume mixture of n-butanol, acetic acid and water;
5) High performance liquid chromatography;
Column; ODS H2151(Senshu Kagaku Co.);
Developing solvent: 5% acetonitrile—0.1% aqueous trifluoroacetic acid;
Flow rate: 1.0 ml/minute;
Retention time: 13.6 minutes.

EXAMPLE 12

Mureidomycin DP from mureidomycin D

The procedure described in Example 9 was repeated, but reacting 100 mg of mureidomycin D and 200 mg of pepsin for hours, to give 11 mg of mureidomycin DP having the following physico-chemical properties:
1) Character and appearance; Amphoteric, colorless powder soluble in water;
2) Molecular weight: 561;
3) Molecular formula; $C_{25}H_{35}N_7O_8$;
4) Thin-layer chromatography: Rf value; 0.13; Adsorbent: Silica gel plate (Merck, Kieselgel 60 $F_{254}$); Developing solvent; a 4:1:2 by volume mixture of n-butanol, acetic acid and water;
5) High performance liquid chromatography;
Column; ODS H2151(Senshu Kagaku Co.);
Developing solvent: 5% acetonitrile—0.1% aqueous trifluoroacetic acid;
Flow rate: 1.0 ml/minute;
Retention time: 9.2 minutes.

EXAMPLE 13

Mureidomycin EP from mureidomycin E

The procedure described in Example 9 Was repeated, but reacting 100 mg of mureidomycin E and 200 mg of pepsin for 24 hours, to give 38 mg of mureidomycin EP having the following physico-chemical properties:
1) Character and appearance: Amphoteric, colorless powder soluble in water;
2) Molecular weight: 514;
3) Molecular formula; $C_{24}H_{30}N_6O_7$;
4) Thin-layer chromatography: Rf value; 0.13; Adsorbent: Silica gel plate (Merck, Kieselgel 60 $F_{254}$); Developing solvent; a 4:1:2 by volume mixture of n-butanol acetic acid and water;
5) High performance liquid chromatography;
Column; ODS H2151(Senshu Kagaku Co.);
Developing solvent: 5% acetonitrile—0.1% aqueous trifluoroacetic acid:
Flow rate: 1.0 ml/minute:
Retention time: 10.1 minutes.

EXAMPLE 14

Mureidomycin FP from mureidomycin F

The procedure described in Example 9 was repeated, but reacting 100 mg of mureidomycin F and 200 mg of pepsin for 24 hours, to give 29 mg of mureidomycin FP having the following physico-chemical properties:
1) Character and appearance; Amphoteric, colorless powder soluble in water;
2) Molecular weight; 514;
3) Molecular formula: $C_{24}H_{30}N_6O_7$;
4) Thin-layer chromatography: Rf value: 0.12; Adsorbent: Silica gel plate (Merck, Kieselgel 60 $F_{254}$); Developing solvent: a 4:1:2 by volume mixture of n-butanol acetic acid and water;
5) High performance liquid chromatography;
Column: ODS H2151(Senshu Kagaku Co.);
Developing solvent: 5% acetonitrile—0.1% aqueous trifluoroacetic acid;
Flow rate: 1.0 ml/minute;
Retention time: 5.3 minutes.

We claim:
1. Compounds having the formula

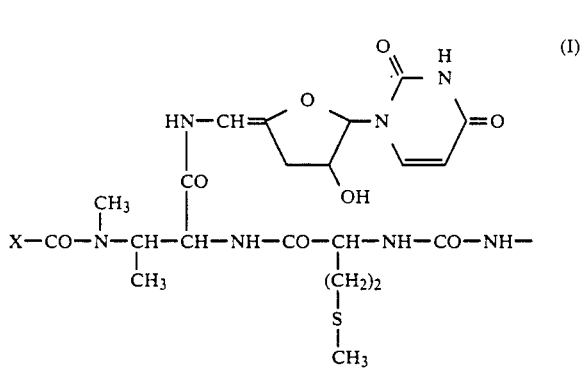

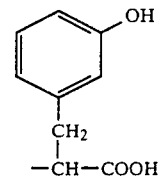

wherein X represents the group

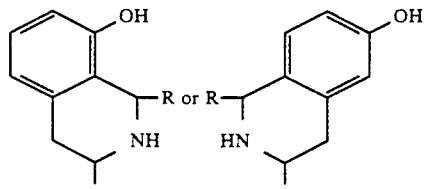

and wherein R represents hydrogen, an alkyl group having from 1 to 10 carbon atoms, an alkenyl group having from 2 to 7 carbon atoms, an alkynyl group having from 3 to 7 carbon atoms, an aryl group having from 6 to 10 carbon atoms, an aralkyl group having from 7 to 10 carbon atoms, or one of the said aryl or aralkyl groups substituted with at least one substituent selected from the group consisting of halogen and alkyl groups having from 1 to 5 carbon atoms; and pharmaceutically acceptable salts and pharmaceutically acceptable esters thereof.

2. The compounds as claimed in claim 1, wherein R represents hydrogen, an alkyl group having from 1 to 3 carbon atoms, an alkenyl group having from 2 to 4 carbon atoms, an alkynyl group having from 3 to 4 carbon atoms, an aryl group having from 6 to 10 carbon atoms, an aralkyl group having from 7 to 8 carbon atoms, or one of the said aryl or aralkyl groups substituted with at least one substituent selected from halogen and alkyl groups having from 1 to 5 carbon atoms; and pharmaceutically acceptable salts and pharmaceutically acceptable esters thereof.

3. The compounds as claimed in claim 1, wherein R represents hydrogen, an alkyl group having from 1 to 10 carbon atoms, a phenyl group, a halophenyl group, or an alkylphenyl group having from 1 to 5 carbon atoms in the alkyl moiety; and pharmaceutically acceptable salts and pharmaceutically acceptable esters thereof.

4. The compounds as claimed in claim 1, wherein R represents hydrogen, an alkyl group having from 1 to 5 carbon atoms or a phenyl group; and pharmaceutically acceptable salts and pharmaceutically acceptable esters thereof.

5. A compound having the formula

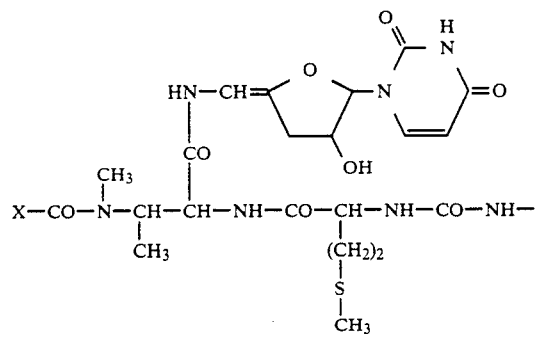

wherein X represents the 8-hydroxy-1,2,3,4-tetrahydroisoquinolin-3-yl group, and pharmaceutically acceptable salts and pharmaceutically acceptable esters thereof.

6. A compound having the formula

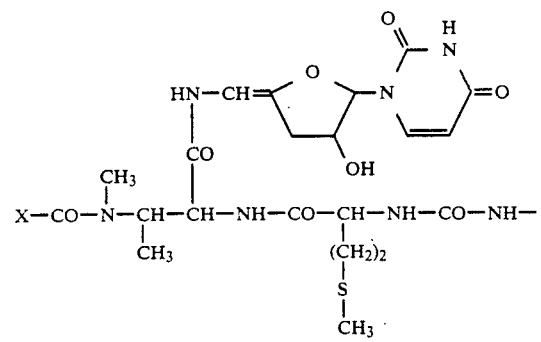

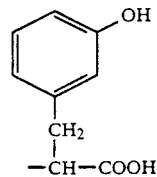

wherein X represents the 6-hydroxy-1,2,3,4-tetrahydroisoquinolin-3-yl group, and pharmaceutically acceptable salts and pharmaceutically acceptable esters thereof.

7. A compound named mureidomycin E, which is obtainable by fermentation from *Streptomyces flavidovirens* SANK 60486 (BIKOKEN JOHKI 1347; FERM BP-1347), and which is characterised by the following physico-chemical properties:

1) Character and appearance: Amphoteric, soluble in water, white powder;
2) Specific rotation: $[\alpha]_D^{25}$ $-34.2°$ (c 1.17, 50% v/v aqueous methanol)
3) Elemental analysis; C, 48.57%; H, 5.35%; N, 11.34%; S, 3.00%—measured as the hydrate;
4) Molecular weight: 852 [high resolution mass spectrum FAB MS: 853.3212 (QM+)] (FAB MS is Fast Atom Bombardment Mass Spectroscopy);
5) Molecular formula; $C_{39}H_{48}N_8O_{12}S$;
6) products resulting from acid hydrolysis: uracil; m-tyrosine; 2-amino-3-N-methylaminobutyric acid; 8-hydroxy-1,2,3,4-tetrahydro-3-isoquinoline carboxylic acid:
7) Ultraviolet absorption spectrum, $\lambda_{max}$nm ($E_1$ $cm^{1\%}$): 258 nm (252) in neutral water; 258 nm (247) in 0.01N aqueous hydrochloric acid; 240 nm (432), 265 nm (235, shoulder) and 295 nm (80, shoulder) in 0.01N aqueous sodium hydroxide; the spectra are shown in FIG. 1 of the accompanying drawings;
8) Infrared absorption spectrum (KBr) $\nu_{max}$ $cm^{-1}$: the spectrum measured in a KBr disk is shown in FIG. 2 of the accompanying drawings;
9) Nuclear magnetic resonance spectrum, δ ppm: the spectrum (270 MHz) was measured in deuterium oxide using tetramethylsilane as external standard and is shown in FIG. 3 of the accompanying drawings (including conformational isomer);
10) Solubility: Soluble in water and methanol, slightly soluble in acetone, and insoluble in ethyl acetate, chloroform and benzene;
11) Color reactions: positive to ninhydrin, sulfuric acid, iodine, ferric chloride and Baeyer reactions;
12) Thin-layer chromatography: Rf value: 0.39; Adsorbent: Silica gel plate (Merck, Kieselgel 60 $F_{254}$); Developing solvent: a 4:2:1 by volume mixture of butanol, propanol and water;
13) High performance liquid chromatography: Column: Aquasil SS 372-N (Senshu Kagaku Co.); Developing solvent: a 200:100:100:40 by volume mixture of chloroform, isopropanol, methanol and water; Flow rate: 1.0 ml/minute; Retention time: 4.7 minutes;

pharmaceutically acceptable salts and pharmaceutically acceptable esters thereof.

8. A compound named mureidomycin F, which is obtainable by fermentation from *Streptomyces flavidovirens* SANK 60486 (BIKOKEN JOHKI 1347; FERM BP-1347), and which is characterised by the following physico-chemical properties:

1) Character and appearance: Amphoteric, soluble in water, white powder;
2) Specific rotation: $[\alpha]_D^{25}$ −40.3° (c 1.05, 50% v/v aqueous methanol);
3) Elemental analysis: C. 50.40%; H, 5.53%; N, 11.20%; S, 2.92%—measured as the hydrate;
4) Molecular weight: 852 [high resolution mass spectrum FAB MS: 853.3180 (QM+)]
5) Molecular formula: $C_{39}H_{48}N_8O_{12}S$;
6) Products resulting from acid hydrolysis: uracil; m-tyrosine; 2-amino-3-N-methylaminobutyric acid; 6-hydroxy-1,2,3,4-tetrahydro-3-isoquinoline carboxylic acid;
7) Ultraviolet absorption spectrum, $\lambda_{max}$ nm ($E_1$ $_{cm}1\%$): 258 nm (232) in neutral water; 258 nm (232) in 0.01N aqueous hydrochloric acid; 240 nm (352), 265 nm (200, shoulder) and 295 nm (64, shoulder) in 0.01N aqueous sodium hydroxide; the spectra are shown in FIG. 4 of the accompanying drawings;
8) Infrared absorption spectrum (KBr) $\nu_{max}$ cm$^{-1}$: the spectrum measured in a KBr disk is shown in FIG. 5 of the accompanying drawings;
9) Nuclear magnetic resonance spectrum, δ ppm: the spectrum (270 MHz) was measured in deuterium oxide using tetramethylsilane as external standard and is shown in FIG. 6 of the accompanying drawings (including conformational isomer);
10) Solubility: Soluble in water and methanol, slightly soluble in acetone, and insoluble in ethyl acetate, chloroform and benzene;
11) Color reactions: positive to ninhydrin, sulfuric acid, iodine, ferric chloride and Baeyer reactions;
12) Thin-layer chromatography: Rf value: 0.34; Adsorbent: Silica gel plate (Merck, Kieselgel 60 $F_{254}$); Developing solvent: a 4:2:1 by volume mixture of butanol, propanol and water;
13) High performance liquid chromatography: Column: Aquasil SS 372-N (Senshu Kagaku Co.); Developing solvent; a 200:100:100:40 by volume mixture of chloroform, isopropanol, methanol and water; Flow rate: 1.0 ml/minute; Retention time: 5.3 minutes;

and pharmaceutically acceptable salts and pharmaceutically acceptable esters thereof.

9. The pharmaceutical composition comprising an effective antibiotic amount of a compound of formula (I), as defined in claim 1, or a pharmaceutically acceptable salt or a pharmaceutically acceptable ester thereof, in admixture with a pharmaceutically acceptable carrier or diluent.

10. The pharmaceutical composition comprising an effective antibiotic amount of mureidomycin E or a pharmaceutically acceptable salt or a pharmaceutically acceptable ester thereof, in admixture with a pharmaceutically acceptable carrier or diluent.

11. The pharmaceutical composition comprising an effective antibiotic amount of mureidomycin F, or a pharmaceutically acceptable salt or a pharmaceutically acceptable ester thereof, in admixture with a pharmaceutically acceptable carrier or diluent.

12. The method for the treatment of prophylaxis of bacterial infections in a human or non-human animal, which comprises administering to said animal an effective antibiotic amount of a compound of formula (I), as defined in claim 1, or a pharmaceutically acceptable salt or a pharmaceutically acceptable ester thereof.

13. The method for the treatment or prophylaxis of bacterial infections in a human or non-human animal, which comprises administering to said animal an effective antibiotic amount of the antibiotic mureidomycin E, or a pharmaceutically acceptable salt or a pharmaceutically acceptable ester thereof.

14. The method for the treatment or prophylaxis of bacterial infections in a human or non-human animal, which comprises administering to said animal an effective antibiotic amount of the antibiotic mureidomycin F, or a pharmaceutically acceptable salt or a pharmaceutically acceptable ester thereof.

15. The compound as claimed in claim 1, wherein the ester is selected from the group consisting of $C_1$-$C_6$-alkyl esters, aralkyl esters, alkoxycarbonylalkyl esters in which the alkoxy and alkyl moieties each have 1 to 4 carbon atoms, alkoxycarbonyloxyalkyl esters in which the alkoxy and alkyl moieties each have 1 to 4 carbon atoms, phthalidyl esters, phthalidyl, phenacyl esters, p-nitrophenacyl ester and (5-methyl-2-oxo-1,3-dioxolen-4yl) methyl esters.

16. The compound as claimed in claim 1, wherein the ester is selected from the group consisting of methyl ester, ethyl ester, propyl ester, isopropyl ester, butyl ester, isobutyl ester, sec-butyl ester, t-butyl ester, pentyl ester, hexyl ester, benzyl ester, p-nitrobenzyl ester, benzhydryl ester, ethoxycarbonylmethyl ester, t-butoxycarbonylmethyl ester, 2-alkoxycarbonyloxyethyl ester and p-nitrophenacyl ester.

17. The compound as claimed in claim 5, wherein the ester is selected from the group consisting of $C_1$-$C_6$-alkyl esters, aralkyl esters, alkoxycarbonylalkyl esters in which the alkoxy and alkyl moieties each have 1 to 4 carbon atoms; alkoxycarbonyloxyalkyl esters in which the alkoxy and alkyl moieties each have 1 to 4 carbon atoms, phthalidyl esters, phenacyl esters, p-nitrophenacyl ester and (5-methyl-2-oxo-1,3-dioxolen-4-yl) methyl esters.

18. The compound as claimed in claim 5, wherein the ester is selected from the group consisting of methyl ester, ethyl ester, propyl ester, isopropyl ester, butyl ester, isobutyl ester, sec-butyl ester, t-butyl ester, pentyl ester, hexyl ester, benzyl ester, p-nitrobenzyl ester, benzhydryl ester, ethoxycarbonylmethyl ester, t-butoxycarbonylmethyl ester, 2-alkoxycarbonyloxyethyl ester and p-nitrophenacyl ester.

19. The compound as claimed in claim 6, wherein the ester is selected from the group consisting of $C_1$-$C_6$-alkyl esters, aralkyl ester, alkoxycarbonylalkyl esters in which the alkoxy and alkyl moieties each have 1 to 4 carbon atoms, alkoxycarbonyloxyalkyl esters in which the alkoxy and alkyl moieties each have 1 to 4 carbon atoms, phthalidyl esters, phenacyl esters, p-nitrophenacyl ester and (5-methyl-2-oxo-1,3-dioxolen-4yl) methyl esters.

20. The compound as claimed in claim 6, wherein the ester is selected from the group consisting of methyl ester, ethyl ester, propyl ester, isopropyl ester, butyl ester, isobutyl ester, sec-butyl ester, t-butyl ester, pentyl ester, hexyl ester, benzyl ester, p-nitrobenzyl ester, benzhydryl ester, ethoxycarbonylmethyl ester, t-butoxycarbonylmethyl ester,, 2-alkoxycarbonyloxyethyl ester and p-nitrophenacyl ester.

21. The compound as claimed in claim 7, wherein the ester is selected from the group consisting of $C_1$-$C_6$-alkyl esters, aralkyl esters, alkoxycarbonylalkyl esters in which the alkoxy and alkyl moieties each have 1 to 4 carbon atoms, alkoxycarbonyloxyalkyl esters in which the alkoxy and alkyl moieties each have 1 to 4 carbon atoms, phthalidyl esters, phenacyl esters, p-nitrophenacyl ester and (5-methyl-2-oxo-1,3-dioxolen-4-yl) methyl esters.

22. The compound as claimed in claim 7, wherein the ester is selected from the group consisting of methyl ester, ethyl ester, propyl ester, isopropyl ester, butyl ester, isobutyl ester, sec-butyl ester, t-butyl ester, pentyl ester, hexyl ester, benzyl ester, p-nitrobenzyl ester, benzhydryl ester, ethoxycarbonylmethyl ester, t-butoxycarbonylmethyl ester, 2-alkoxycarbonyloxyethyl ester and p-nitrophenacyl ester.

23. The compound as claimed in claim 8, wherein the ester is selected from the group consisting of $C_1$–$C_6$-alkyl esters, aralkyl esters, alkoxycarbonylalkyl esters in which the alkoxy and alkyl moieties each have 1 to 4 carbon atoms, alkoxycarbonyloxyalkyl esters in which the alkoxy and alkyl moieties each have 1 to 4 carbon atoms, phthalidyl esters, phenacyl esters, p-nitrophenacyl ester and (5-methyl-2-oxo-1,3-dioxolen-4-yl) methyl esters.

24. The compound as claimed in claim 8, wherein the ester is selected from the group consisting of methyl ester, ethyl ester, propyl ester, isopropyl ester, butyl ester, isobutyl ester, sec-butyl ester, t-butyl ester, pentyl ester, hexyl ester, benzyl ester, p-nitrobenzyl ester, benzhydryl ester, ethoxycarbonylmethyl ester, t-butoxycarbonylmethyl ester, 2-alkoxycarbonyloxyethyl ester and p-nitrophenacyl ester.

25. The method of claim 12, wherein said compound is administered in a daily dose of 0.1 to 10 grams.

26. The method of claim 13, wherein said mureidomycin E compound is administered in a daily dose of 0.1 to 10 grams.

27. The method of claim 14, wherein said mureidomycin F is administered in a daily dose of 0.1 to 10 grams.

28. The method of claim 13, wherein said antibiotic is mureidomycin E.

29. The method of claim 14, wherein said antibiotic is mureidomycin F.

30. The compound of claim 7 which is mureidomycin E.

31. The compound of claim 8 which is mureidomycin F.

* * * * *

UNITED STATES PATENT AND TRADEMARK OFFICE
CERTIFICATE OF CORRECTION

PATENT NO. : 5,041,423
DATED : August 20, 1991
INVENTOR(S) : HANEISHI et al

It is certified that error appears in the above-identified patent and that said Letters Patent is hereby corrected as shown below:

Column 1, lines 38-39, delete "and now abandoned".

Column 9, line 45, change "$[\alpha_D^{25}$" to read --$[\alpha]_D^{25}$--.

Column 10, line 23 change "$[\alpha_D^{25}$" to read --$[\alpha]_D^{25}$--.

Column 15, line 59, before "above", insert --500 ml of medium A, which has the composition described--.

Column 26, line 30 (Claim 7), change "products" to read --Products--.

Column 26, line 48 (Claim 7), change "10Solubility:" to read --10) Solubility:--.

Column 28, line 19 (Claim 15), delete "phthalidyl," (second occurrence).

Signed and Sealed this

Fifth Day of October, 1993

Attest:

BRUCE LEHMAN

Attesting Officer

Commissioner of Patents and Trademarks